US011360092B2

(12) United States Patent
Shroyer et al.

(10) Patent No.: US 11,360,092 B2
(45) Date of Patent: Jun. 14, 2022

(54) KERATIN 17 AS A BIOMARKER FOR BLADDER CANCER

(71) Applicants: THE RESEARCH FOUNDATION FOR THE STATE UNIVERSITY OF NEW YORK, Albany, NY (US); KDX DIAGNOSTICS, INC., Campbell, CA (US)

(72) Inventors: Kenneth R. Shroyer, Setauket, NY (US); Luisa F. Escobar-Hoyos, New York, NY (US); Nam Kim, San Jose, CA (US)

(73) Assignees: The Research Foundation for The State University of New York, Albany, NY (US); KDx Diagnostics, Inc., Cambell, CA (US)

( * ) Notice: Subject to any disclaimer, the term of this patent is extended or adjusted under 35 U.S.C. 154(b) by 195 days.

(21) Appl. No.: 16/321,577

(22) PCT Filed: Aug. 4, 2017

(86) PCT No.: PCT/US2017/045421
§ 371 (c)(1),
(2) Date: Jan. 29, 2019

(87) PCT Pub. No.: WO2018/027091
PCT Pub. Date: Feb. 8, 2018

(65) Prior Publication Data
US 2020/0284794 A1 Sep. 10, 2020

Related U.S. Application Data

(60) Provisional application No. 62/371,286, filed on Aug. 5, 2016.

(51) Int. Cl.
*G01N 33/574* (2006.01)
*G01N 33/569* (2006.01)
*C12Q 1/6886* (2018.01)

(52) U.S. Cl.
CPC . *G01N 33/57407* (2013.01); *G01N 33/56966* (2013.01); *C12Q 1/6886* (2013.01); *C12Q 2600/158* (2013.01); *G01N 2333/4742* (2013.01)

(58) Field of Classification Search
CPC ....... G01N 33/57407; G01N 33/56966; G01N 2333/4742
See application file for complete search history.

(56) References Cited

U.S. PATENT DOCUMENTS

| | | |
|---|---|---|
| 6,207,380 B1 | 3/2001 | Billing-Medel et al. |
| 6,350,571 B1 | 2/2002 | Lokeshwar et al. |
| 7,081,516 B2 | 7/2006 | Markowitz |
| 7,118,912 B2 | 10/2006 | Markowitz |
| 7,183,057 B2 | 2/2007 | Benson |
| 7,229,774 B2 | 6/2007 | Chinnaiyan et al. |
| 7,465,553 B2 | 12/2008 | Polyak et al. |
| 7,531,634 B2 | 5/2009 | Getzenberg |
| 7,592,145 B2 | 9/2009 | Bao et al. |
| 7,794,926 B2 | 9/2010 | Altieri et al. |
| 7,951,549 B2 | 5/2011 | Haley et al. |
| 8,007,995 B2 | 8/2011 | Finn et al. |
| 8,071,815 B2 | 12/2011 | Indra et al. |
| 8,124,331 B2 | 2/2012 | Martinez et al. |
| 8,153,370 B2 | 4/2012 | Adami et al. |
| 8,268,568 B2 | 9/2012 | Markowitz |
| 8,377,636 B2 | 2/2013 | Haley et al. |
| 8,465,912 B2 | 6/2013 | Kan |
| 8,486,648 B2 | 7/2013 | Livingston et al. |
| 8,642,834 B2 | 2/2014 | Kan et al. |
| 8,673,572 B2 | 3/2014 | Tran |
| 8,741,582 B2 | 6/2014 | Datta et al. |
| 8,912,159 B2 | 12/2014 | Iragavarapu-Charyulu et al. |
| 9,040,667 B2 | 5/2015 | Liao et al. |
| 9,702,009 B2 | 7/2017 | Guilford |
| 9,789,159 B2 | 10/2017 | Dhar-Mascareno et al. |
| 9,834,821 B2 | 12/2017 | Aharonov et al. |
| 9,840,551 B2 | 12/2017 | Shen et al. |
| 10,024,859 B2 | 7/2018 | Guilford |
| 10,047,399 B2 | 8/2018 | Ting et al. |
| 10,139,412 B2 | 11/2018 | Vadasz et al. |
| 10,539,566 B2 | 1/2020 | Narain et al. |
| 10,845,365 B2 | 11/2020 | Datta et al. |
| 11,092,603 B2 | 8/2021 | Shroyer et al. |
| 11,237,169 B2 | 2/2022 | Hewitt et al. |
| 2009/0047212 A1* | 2/2009 | Berman ................ A61P 35/00 424/1.49 |
| 2016/0187341 A1 | 6/2016 | Shroyer et al. |

FOREIGN PATENT DOCUMENTS

JP 2010-527605 A 8/2010

OTHER PUBLICATIONS

Guelstein et al. Immunochemical localization of cytokeratin 17 in transitional cell carcinomas of human urinary tract. Virchows Archiv B Cell Pathol. 64: 1-5 (1993)- IDS.*
Somji et al. Comparison of expression patterns of keratin 6, 7, 16, 17, and 19 within multiple independent isolates of As+3 and Cd+ 2-induced bladder cancer. Cell Biol Toxicol 27: 381-396 (2011)-IDS.*
European Communication dated Jan. 13, 2021 received in European Application No. 17 837 731.3.

(Continued)

*Primary Examiner* — Gailene Gabel
(74) *Attorney, Agent, or Firm* — Scully, Scott, Murphy & Presser, P.C.

(57) ABSTRACT

The current disclosure provides methods for detecting and analyzing K17 expression in a bladder sample obtained from a subject. The current disclosure also pertains to methods and kits for identifying a mammalian subject with bladder cancer by detecting the expression of K17 in a sample. The present methods include both cell-based and cell-free methods for determining the level of keratin 17 in a sample obtained from the bladder of a subject.

Figure 1:
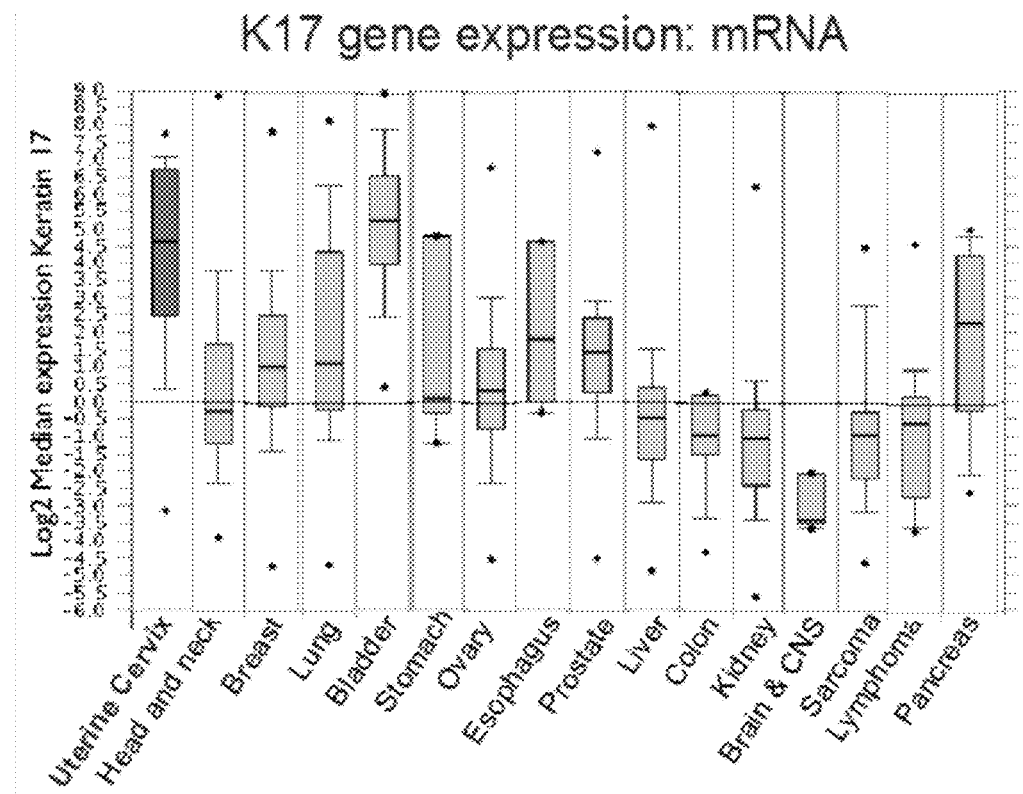

10 Claims, 8 Drawing Sheets
Specification includes a Sequence Listing.

(56) References Cited

OTHER PUBLICATIONS

European Office Action dated Sep. 4, 2020 received in European Application No. 17 837 731 3.
International Search Report dated Jan. 5, 2018 issued in PCT/US2017/045421.
Laguna, P. et al., "Keratin Expression Profiling of Transitional Epithelium in the Painful Bladder Syndrome/Interstitial Cystitis", American Journal of Clinical Pathology (Jan. 2006), vol. 125, No. 1, pp. 105-110.
Guelstein, V. et al., "Immunohistochemical localization of cytokeratin 17 in transitional cell carcinomas of the human urinary tract", Virchows Archiv. B, Cell Pathology including Molecular Pathology (Dec. 1993), vol. 64, No. 1, pp. 1-5.
Tetu, B., "Diagnosis of urothelial carcinoma from urine", Modern Pathology (Jun. 2009), vol. 22, No. 12, pp. S53-S59.
Chung, BM, et al., "Regulation of C-X-C chemokine gene expression by keratin 17 and hnRNP K in skin tumor keratinocytes", The Journal of Cell Biology (Mar. 2, 2015), Epub Feb. 23, 2015, vol. 208, No. 5, pp. 613-627.
Abbott Molecular, Inc., Urovysion Bladder Cancer Kit (package insert) Aug. 2014; [retrieved on Sep. 29, 2017], retrieved from the Internet: <URL https://www.molecular.abbott/sal/en-us/staticAssets/UroVysion%20package%20insert%20R6% 20-%20watermark.pdf>; p. 1, 1st col., 1st paragraph.
Bournet, B., et al., "Gene expression signature of advanced pancreatic ductal adenocarcinoma using low density array on endoscopic ultrasound-guided fine needle aspiration samples", Pancreatology (Jan.-Feb. 2012), Epub Dec. 2011, vol. 12, No. 1, pp. 27-34.
Babu S. et al., "Keratin 17 is a Sensitive and Specific Biomarker and Urothelial Neoplasia", Modem Pathology 32 (5):717-724 (Nov. 2019).
Guelstein V.I. et al., "Immunohistochemical Localization of Cytokeratin 17 in Transitional Cell Carcinomas of the Human Urinary Tract", Virchows Archiv B Cell Pathology 64(1):1-5 (Nov. 30, 1993).
Laguna P. et al., "Keratin Expression Profiling of Transitional Epithelium in the Painful Bladder Syndrome/Interstitial Cystitis", Am J Clin Pathol 125(1):105-110 (Jan. 1, 2006).
MacDonald D. et al., "MP-04.06: Gene Expression Profile of Urine Sediment for the Non-Invasive Diagnosis of Bladder Cancer", Urology 70(Supplment 3A):59-60 (Sep. 1, 2007).
Somji S. et al., "Comparison of Expression Patterns of Keratin 6, 7, 16, 17, and 19 Within Multiple Independent Isolates of As+3- and Cd+2-Induced Bladder Cancer", Cell Biol Toxicol 27(6):381-396 (Sep. 17, 2011).
Extended Supplementary Search Report dated Feb. 24, 2020 received in European Application No. 17 83 7731.3.
Abbott Molecular, Inc., "Urovysion Bladder Cancer Kit", 15 pages, (Aug. 2014).
Bournet B. et al., "Gene Expression Signature of Advanced Pancreatic Ductal Adenocarcinoma Using Low Density Array on Endoscopic Ultrasound-Guided Fine Needle Aspiration Samples", Pancreatology 12:27-34 (2012).
Carmack A.J.K. et al., "The Diagnosis and Staging of Bladder Cancer: From RBCs to TURs", Urology 67(Suppl 3A):3-10 (Mar. 2006).
Chung B M et al., "Regulation of C-X-C Chemokine Gene Expresison by Keratin 17 and hnRNP K in Skin Tumor Keratinocytes", J. Cell Biol. 208(5):613-627 (2015).
Edge S.B et al., "The American Joint Committee on Cancer: the 7th Edition of the AJCC Cancer Staging Manual and the Future of TNM", Annals of Surgical Oncology 17:1471-1474 (2010).
Escobar-Hoyos L.F. et al., "Keratin-17 Promotes p27KIP1 Nuclear Export and Degradation and Offers Potential Prognostic Utility", Cancer Research 75(17):3650-3662 (Sep. 1, 2015).
Escobar-Hoyos L.F. et al., "Keratin 17 in Premalignant and Malignant Squamous Lesions of the Cervix: Proteomic Discovery and Immunohistochemical Validation as a Diagnostic and Prognostic Biomarker", Modern Pathology 27:621-630 (2014).
Grossman H.B. et al., "Detection of Bladder Cancer Using a Point-of-Care Proteomic Assay", JAMA 293 (7):810-816 (Feb. 16, 2005).
Guelstein V.I. et al., "Immunohistochemical Localization of Cytokeratin 17 in Transitional Cell Carcinomas of the Human Urinary Tract", Virchows Archiv B Cell Pathol 64(1):1-5 (Dec. 1993).
Kaufman D S et al., "Bladder Cancer", Lancet 374:239-249 (2009).
Laguna P. et al., "Keratin Expression Profiling of Transitional Epithelium in the Painful Bladder Syndrome/Interstitial Cystitis", Am J Clin Pathol. 125:105-110 (2006).
Ruifrok A.C. et al., "Quantification of Histochemical Staining by Color Deconvolution", Analytical and Quantitative Cytology and Histology 23:291-299 (2001).
Schmittgen TD et al., "Analyzing Real-Time PCR Data by the Comparative CT Method", Nature Protocols 3 (6):1101-1108 (2008).
Schneider CA et al., "NIH Image to ImageJ: 25 Years of Image Analysis", Nature Methods 9(7):671-675 (Jul. 2012).
Têtu B., "Diagnosis of Urothelial Carcinoma from Urine", Modem Pathology 22:S53-S59 (2009).
Youden W.J., "Index for Rating Diagnostic Tests", Cancer 3:32-35 (Jan. 1950).
NCBI Reference Sequence No. NG_008625.1 (7 pages) (Jan. 9, 2019).
NCBI Reference Sequence No. NM_000422.3 (8 pages) (Jan. 9, 2019).
NCBI Reference Sequence No. NP_000413.1 (6 pages) (Jan. 9, 2019).
International Search Report dated Jan. 5, 2018 received in International Application No. PCT/US17/45421.
Yokono H. et al., "Significance of Cytokeratin 17 Expression in Bladder Transitional Cell Carcinoma", The Journal of the Japanese Society of Clinical Cytology 38(2):571 (1999) . Statement of relevancy in 2019-527778 Rejection.
Japanese Notice of Reasons for Rejection dated Jun. 7, 2021 received in Japanese Application No. 2019-527778, together with an English-language translation.
European Office Action dated Apr. 21, 2021 received in European Application No. 17 837 731.3.
Ecke T.H. et al., "UBC® Rapid Test for Detection of Carcinoma In Situ for Bladder Cancer", Tumor Biology, pp. 1-7 (May 2017).
He X. et al., "Differentiation of a Highly Tumorigenic Basal Cell Compartment in Urothelial Carcinoma", Stem Cells 27(7):1487-1495 (Jul. 2009).
Moll R. et al., "Cytokeratins in Normal and Malignant Transitional Epithelium", American Journal of Pathology 132 (1):123-144 (Jul. 1988).
Ostergaard M. et al., "Proteome Profiling of Bladder Squamous Cell Carcinomas" Identification of Markers That Define Their Degree of Differentiation, Cancer Research 57:4111-4117 (Sep. 15, 1997).
Southgate J. et al., "Cytokeratin Expression Patterns in Normal and Malignant Urothelium: A Review of the Biological and Diagnostic Implications", Histology and Histopathology 14:657-664 (1999).
Korean Office Action dated Sep. 27, 2021 received in Korean Application No. 10-2019-7006516, together with an English-language translation.
Japanese Decision of Rejection dated Mar. 14, 2022 received in Japanese Application No. 2019-527778, together with an English-language translation.

* cited by examiner

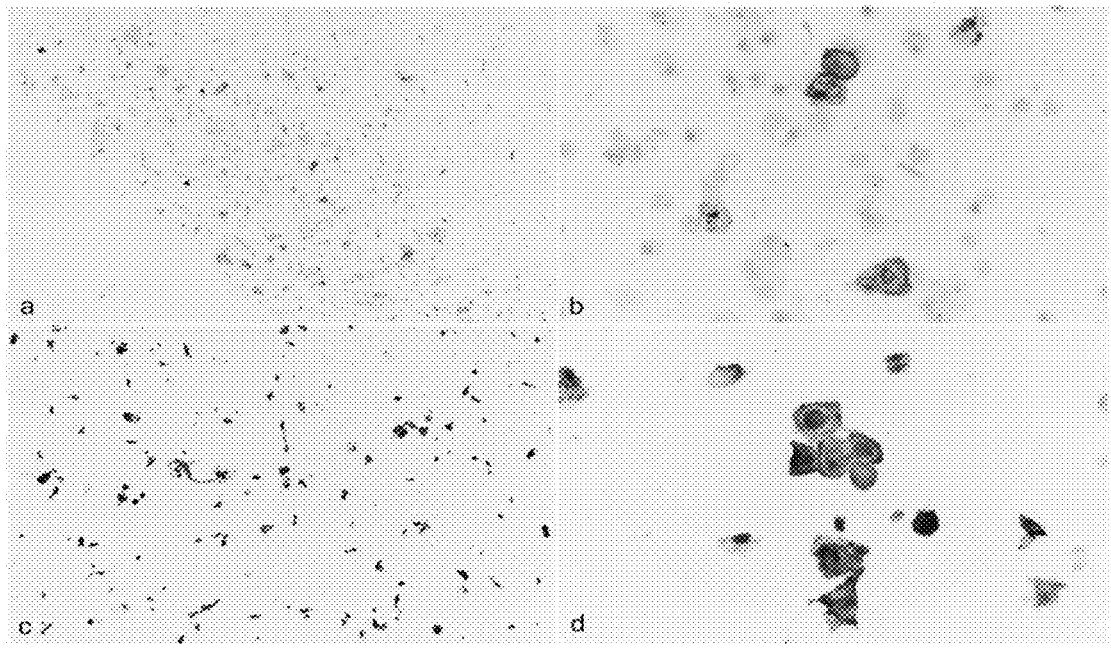
FIGS. 3A-D

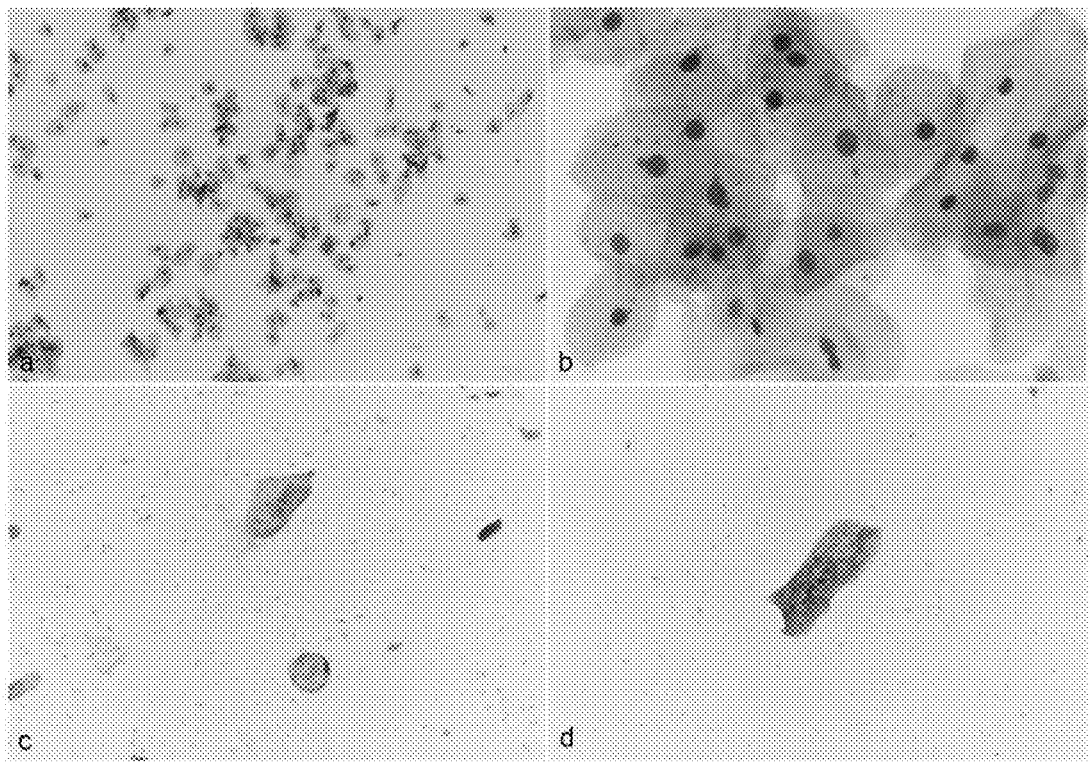
FIGS. 4A-D

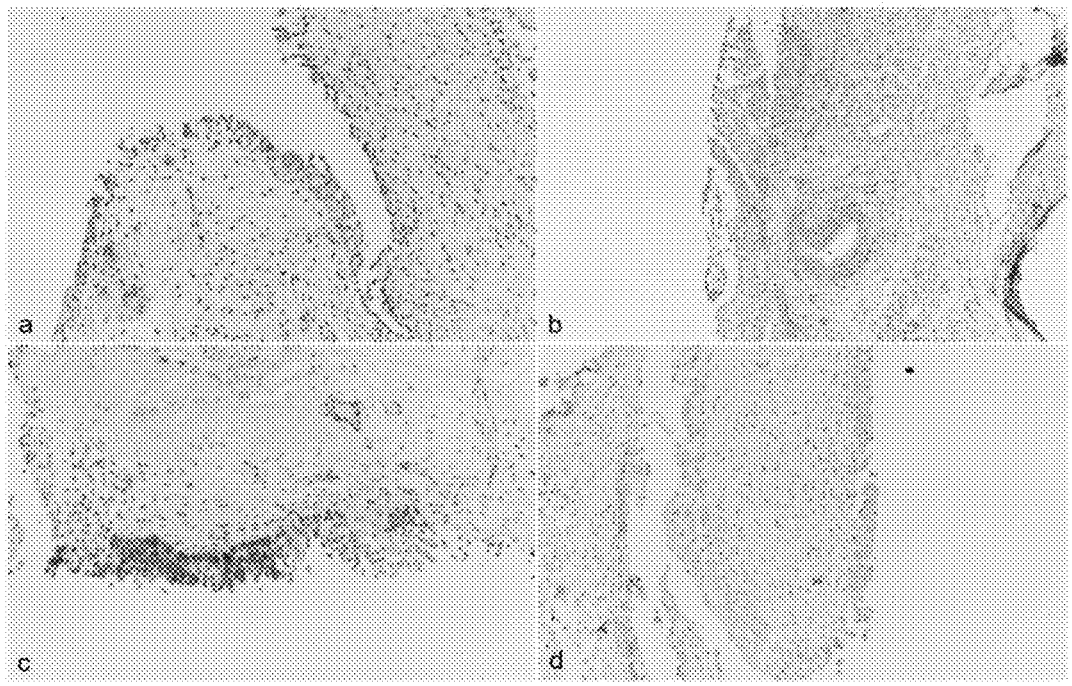
FIGS. 5A-D

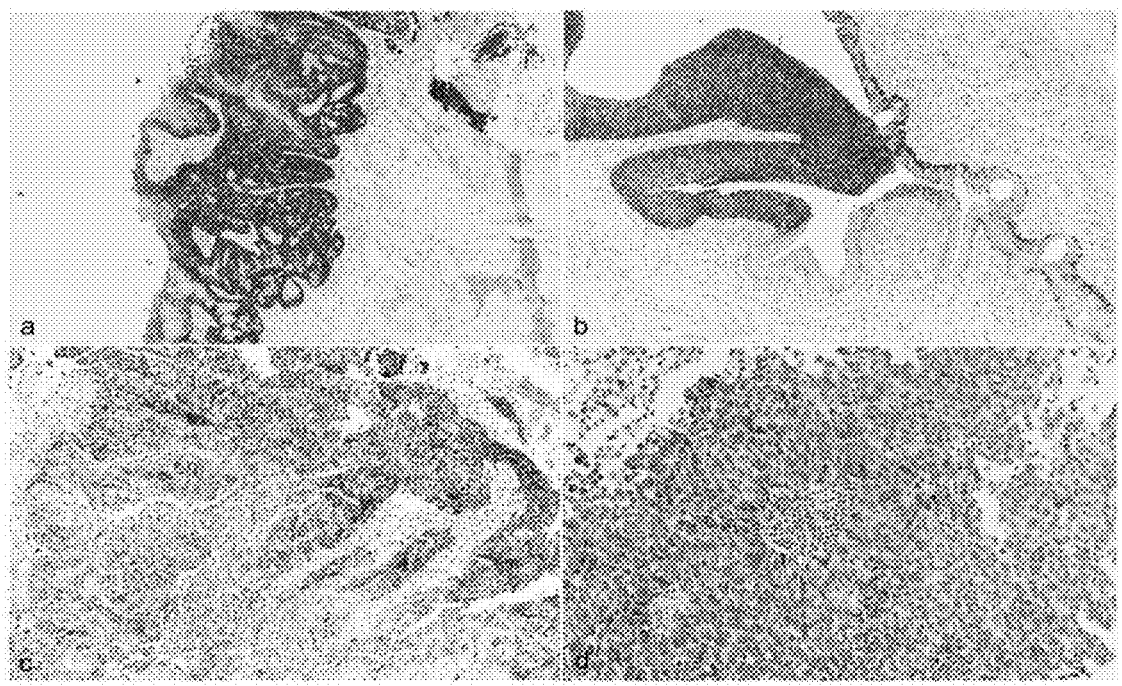
FIGS. 6A-D

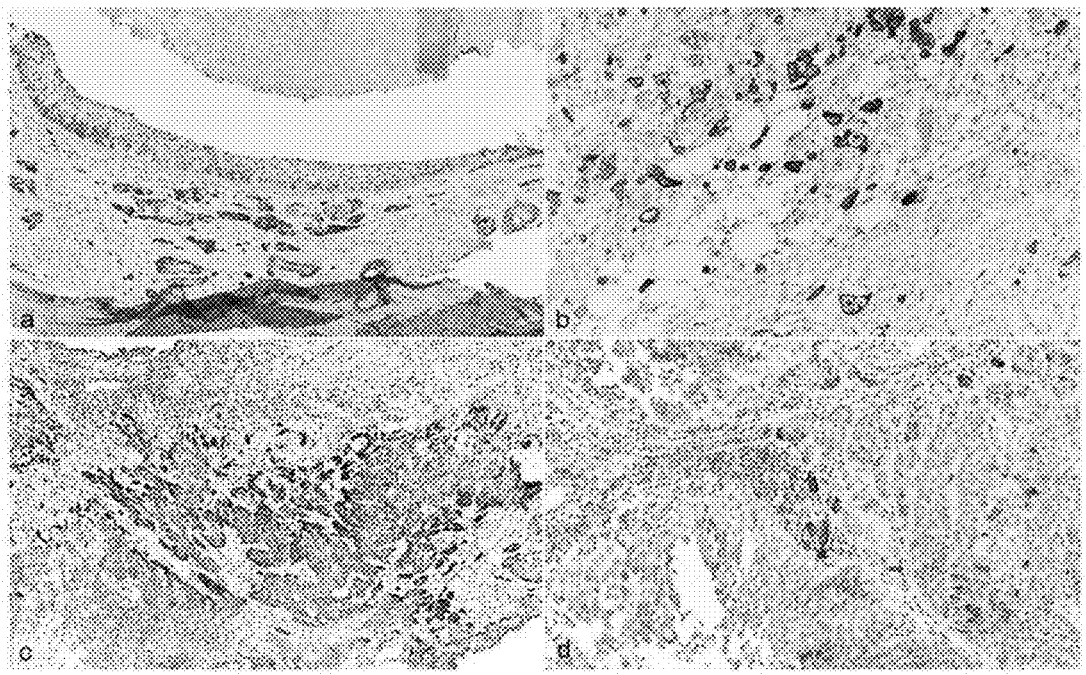
FIGS. 7A-D

A
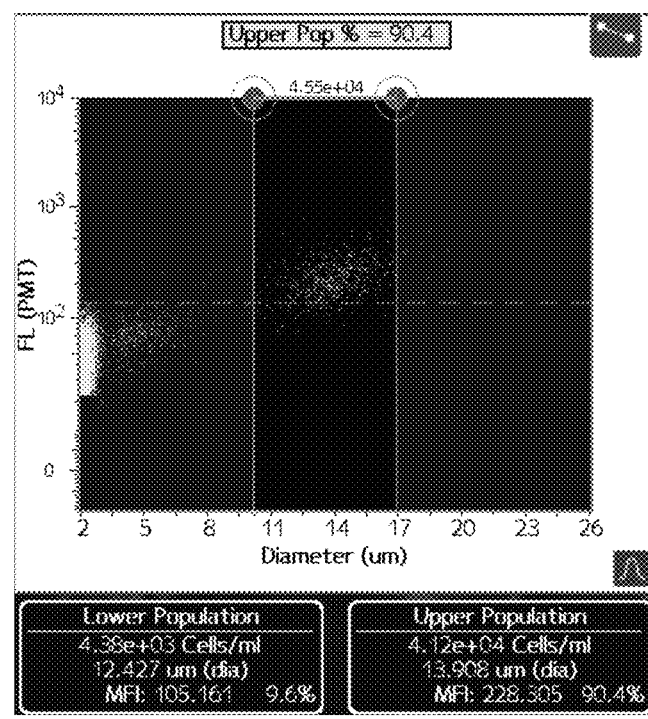
B
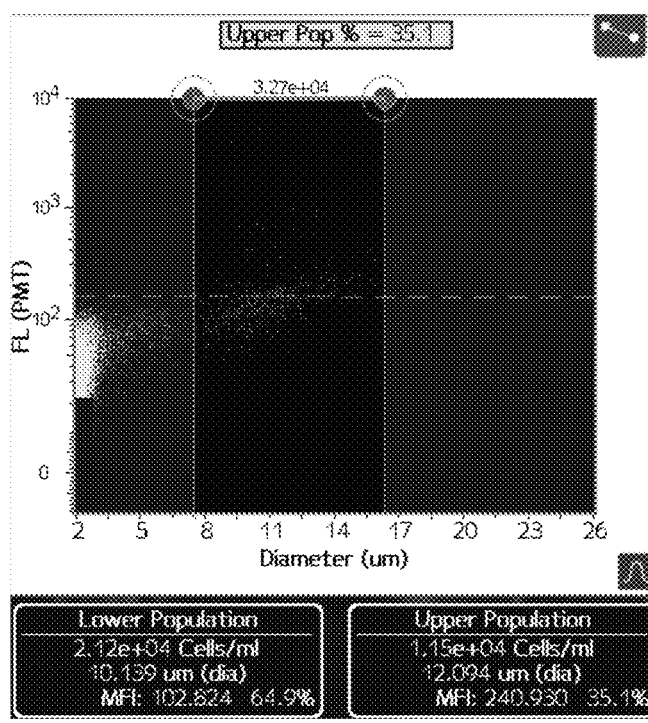
FIGS. 8A-B

KERATIN 17 AS A BIOMARKER FOR BLADDER CANCER

CROSS REFERENCE TO RELATED APPLICATIONS

The present application claims the benefit of priority from U.S. Provisional Application No. 62/371,286, filed on Aug. 5, 2016, the content of which is incorporated herein by reference in its entirety.

FIELD OF THE DISCLOSURE

The current disclosure relates to a method for detecting the amount of keratin 17 in a sample obtained from a subject. The present methods can be used to diagnose bladder cancer in a subject. The methods of the present disclosure can be practiced with tissue biopsies, and cell-based as well as cell-free samples, such as urine samples. The current disclosure further provides methods suitable for determining the presence or absence of K17 in urine, which may or may not contain intact cells, as well as, methods for estimating expression levels of cytokeratin 17 in bladder tissue via detection of K17 protein or mRNA in the cell-free portion of urine of a subject to determine the presence of bladder cancer in that subject.

BACKGROUND

Bladder cancer is the fourth most common malignancy in men and accounts for about 5% of all newly diagnosed cancers in the United States. See American Cancer Society. Cancer Facts & FIGS. 2016. Atlanta, Ga.: American Cancer Society (2016). About half of all bladder cancers are first identified in the lining of the bladder wall [i.e., the urothelium (also known as the transitional epithelium)] and are deemed non-invasive or in situ cancers or urothelial carcinoma (a.k.a. transitional cell carcinomas). See Grossman, H B, et al. *JAMA*. (2005) 293:810-816. About 1 in 3 bladder cancer patients exhibit invasion of the cancer into the underling muscular layers of the bladder wall. Advances in treatment modalities have led to increased survival rates for subjects diagnosed early (i.e., stage 0 or stage 1 bladder cancer), with an average five-year survival rate of subjects with early diagnosis between 85-98% [American Cancer Society. Cancer Facts & Figures 2016. Atlanta, Ga.: American Cancer Society (2016)]. Conversely, late stage diagnosis results in a much more bleak outcome, whereby subjects diagnosed with stage II or stage III bladder cancer have an average five-year survival rate of between 45% and 65%. See Kaufman D S, et al. *Lancet*. (2009) 374:239-249; American Cancer Society. Cancer Facts & FIGS. 2016. Atlanta, Ga.: American Cancer Society (2016); and Soloway Miss. *Urology*. (2006) 67: 3-10.

Current methods to detect bladder cancer include urinalysis (i.e., the detection of blood in the urine), and a variety of commercial tests are used: Immunocyt™, NMP22 BladderChek®, the BTAstat® Test, and the UroVysion® Bladder Cancer Kit. Immunocyt™ examines the urine of a subject for the presence of mucin and carcinoembryonic antigen (CEA). The NMP22 BladderChek® screen determines whether a specific protein, NMP22 is present in the urine of a subject. The BTAstat® Test is designed to detect human complement factor H related protein (hCFHrp) as a cancer biomarker, which is relatively sensitive for detection of high grade urothelial carcinoma but generally unable to detect low grade lesions (i.e., stage 0–I bladder cancers), which provide the best chance for cure. The UroVysion® Bladder Cancer Kit tests for aneuploidy of chromosomes 3, 7, 17, and loss of the 9p21 locus via fluorescence in situ hybridization (FISH) in urine specimens from subjects suspected of having bladder cancer. Like the BTAstat® Test, UroVysion® is unable to detect low grade tumors of the bladder mucosa effectively, because most low grade tumors are diploid and so test negative with the UroVysion® Bladder Cancer Kit test.

Thus, there is an unmet need to identify novel a diagnostic biomarker that can be used in conjunction with existing treatment methods to determine whether a subject has or continues to have bladder cancer, so that patients in need of treatment can be identified at an early stage. Such methodology would be especially advantageous if it could be: non-invasive, deployed on state of the art diagnostic test systems capable of running multiple tests and/or multiple samples at a time. The methods of the present disclosure address these unmet needs and enable more effective treatment and better patient outcomes and survival time than existing tests.

Keratin 17 (K17, KRT17, or cytokeratin 17), a member of the intermediate filament cytoskeleton family, has been identified as a prognostic and diagnostic biomarker for certain specific cancers, i.e., pancreatic and cervical cancer. See Escobar-Hoyos, L. F., et al. *Modern pathology* (2014) 27(4):621-630. However, the current disclosure identifies that K17 is not overexpressed in all cancers. For example, FIG. 1 clearly shows that while K17 is elevated (highly expressed) in certain cancers, such as cervical cancer and pancreatic cancer, K17 is not highly expressed in many other cancers, such as liver, colon, kidney, brain and lymph node cancers. K17 expression in cancer generally is organ and tumor type specific. Notably, the present disclosure identifies, for the first time, that elevated levels of K17 expression can be detected in bladder tissue of subjects having bladder cancer, compared to K17 expression levels determined from bladder tissue and urine samples of a healthy subject to enable reliable diagnostic testing for bladder cancer via detection of K1.7.

The current disclosure identifies and validates K17's utility as a diagnostic bladder cancer biomarker and provides highly sensitive methods for detecting bladder cancer in a subject. The methods are also advantageous for use in patients not previously known to have bladder cancer for whom a non-invasive, inexpensive test would provide an unexpected advance over existing diagnostics, which require expensive and invasive procedures to verify that the patient has bladder cancer.

SUMMARY OF THE DISCLOSURE

The current disclosure reveals that keratin 17 is a biomarker for diagnosing bladder cancer, including early stage bladder cancers, Which have the best potential for a positive treatment outcome. The present disclosure also reveals that a reliable, non-invasive bladder cancer diagnostic is possible using voided urine. For example, the data herein show that an improved diagnoses can be made on the basis of a urine test alone, by simply reducing the amount of "false negative" readings that plague current non-invasive test methods. The data provided herein also shows that K17 levels were increased (when compared to control samples) in subjects with early stage and high grade bladder cancers, but absent or detected at low levels in normal benign bladder mucosa (i.e., non-cancerous control tissue). Taken together, the current disclosure shows, for the first time, that increased K17 expression is a critical event in the development and progression of bladder cancer and that K17 expression can be measured as a diagnostic indicator of bladder cancer in a subject.

Therefore, in one aspect of the present disclosure, a method for determining the amount of K17 in a subject is provided. In certain embodiments the subject has bladder cancer or may have bladder cancer. In an exemplary embodiment of the present method, a sample of bladder cells is obtained from a subject; and the sample is then labeled to detect the expression of K17 in the sample. In certain embodiments, the presence of K17 is detected through binding of an antibody to a K17 protein in the sample. In another embodiment, presence of K17 is detected by measuring a level of K17 mRNA in a sample, such as by RT-PCR. In other embodiments, K17 expression detected in a sample and compared to that of a control sample (e.g., reference samples or standard) and when K17 levels are increased above that of the control sample the subject has bladder cancer. In certain embodiments, the sample is a bladder tissue biopsy, formalin-fixed paraffin-embedded tissue sample, or a urine sample. In some embodiments, the control sample is benign bladder mucosa, urothelial cells or transitional epithelial cells from a healthy subject. In other embodiments, the control sample is a standard, which may be a reference sample that contains a known amount of K17 protein or nucleic acid or may simply be a readout or instruction that provides a positive, negative, or no result based on a specific amount of K17 protein or nucleic acid detected in a sample. In other embodiments, the sample is urine, and the urine will contain one or more bladder or bladder cancer cells. In some embodiments, the sample will be known not to contain cells. In specific embodiments, the bladder cancer detected is urothelial carcinoma. In certain embodiments, the urothelial carcinoma is a papillary cancer, such as papillary urothelial neoplasm of low-malignant potential (PUNLMP), low grade papillary urothelial carcinoma (LG), high grade papillary urothelial carcinoma (HG), or transitional-urothelial carcinoma. In other embodiments, the bladder cancer detected is a flat carcinoma, such as flat urothelial carcinoma in situ (a non-invasive flat urothelial carcinoma) of the bladder. In yet other embodiments, the bladder cancer detected is invasive cancer such as, for example, invasive urothelial cell carcinoma. In certain embodiments, the bladder cancer detected is squamous cell carcinoma, adenocarcinoma, small cell carcinoma or sarcoma. In some embodiments of the present methods, the presence or absence or level of K17 expression in a sample is determined by immunohistochemical staining or immunocytochemical analysis or by mRNA detection.

In another aspect of the present disclosure, a method for detecting K17 expression in a cell-free sample is provided. In certain embodiments, the subject has bladder cancer or may have bladder cancer. In an exemplary embodiment of the present method, a sample is voided urine obtained from a subject. In other embodiments, the voided urine sample contains no cells or has been processed such that all cells would have been removed from said sample. In specific embodiments, the cell-free urine sample is obtained from a subject; and the sample is then contacted with an anti-K17 antibody to detect the amount of K17 in the sample. Here, the amount of K17 in the sample will reflect the amount of K17 in the bladder of a subject. In certain embodiments, the presence of K17 is detected through binding of an antibody to a K17 protein in the sample or through mass spectrometry. In certain embodiments, the amount of K17 determined by detecting K17 mRNA in the sample. In some embodiments, the methods can be qualitative (i.e., any amount of detected K17 in a samples indicative of bladder cancer) or quantitative (only amounts above a predetermined level are indicative of a subject having bladder cancer). In quantitative embodiments, K17 expression is determined based on the amount of K17 protein or K17 mRNA detected in a sample as compared to that of a control sample, and when K17 levels are increased above that of the control sample, the subject has bladder cancer. In some embodiments, the control sample is urine from a healthy subject (or subjects) or a solution comprising a known amount of K17 protein or mRNA or simply a known amount or a standard set to a specific amount. In specific embodiments, the bladder cancer detected is urothelial carcinoma. In certain embodiments, the urothelial carcinoma detected is a papillary cancer, such as papillary urothelial neoplasm of low-malignant potential (PUNLMP), low grade papillary urothelial carcinoma (LG), or high grade papillary urothelial carcinoma (HG). In other embodiments, the bladder cancer detected is a flat carcinoma, such as flat carcinoma in situ or non-invasive flat urothelial carcinoma of the bladder. In yet other embodiments, the bladder cancer detected is invasive cancer such as, for example, invasive urothelial or transitional cell carcinoma. In certain embodiments, the bladder cancer detected is squamous cell carcinoma, adenocarcinoma, small cell carcinoma or sarcoma. In some embodiments of the present methods, the level of K17 expression in a sample is determined by ELISA. In other embodiments of the present methods, K17 expression levels are determined by detecting the amount of K17 snRNA in bladder cells or urine.

BRIEF DESCRIPTION OF THE DRAWINGS AND TABLES

FIG. 1: Keratin 17 expression varies in different types of cancers. RNA expression data, evaluated by data-mining TCGA Data Portal from the National Cancer Institute. The histogram shows a log-scale representation of K17 expression for a certain types of cancers that have elevated K17 expression, such as cervical, bladder and pancreatic cancer. The chart further shows that many types of cancers, such as colon, liver, brain and lymphatic cancers, express relatively low levels of K17.

Figure 2:
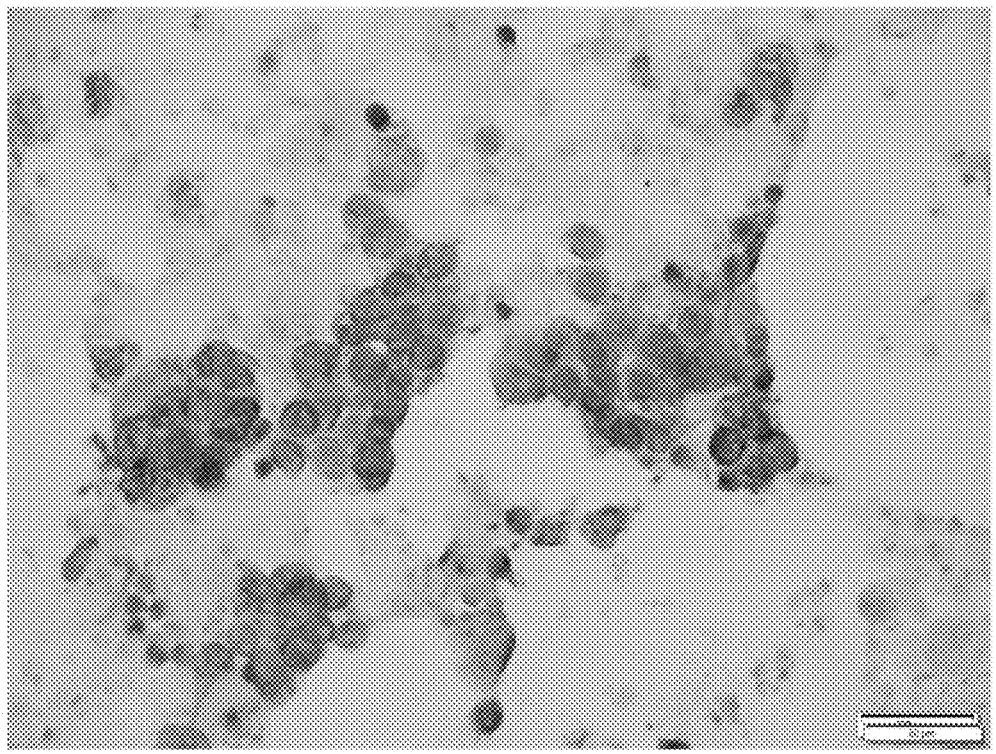

FIG. 2: Immunocytochemical localization of K17 in urine cytology samples. Keratin 17 expression can be shown by the detection of labeled, cytoplasmic K17 (darker cells), whereas other non-cancerous cells are devoid of K17 labeling (normal, unlabeled cells).

FIGS. 3A-D: Keratin 17 urine immunocytochemistry. (a), K17 staining in rare benign cells, 4× magnification; (b), K17 staining in rare benign cells, 40× magnification; (c), increased (2+) K17 staining, 4× magnification; (d), increased (2+) K17 staining, 20× magnification. In rare instances, K17 was sparsely detected in benign cells from normal urine cytology specimens (a, b), but K17 staining was strongly positive in urothelial cells from subjects with urothelial carcinoma (c, d).

FIGS. 4A-D: Keratin 17 immunocytochemistry. (a, b) most normal squamous and urothelial cells (c, d) are negative for K17, i.e., exhibit no keratin 17 staining.

FIGS. 5A-D: Bladder Histology. (a, b, d) only faint focal staining for K1.7 was detected in benign bladder mucosa (c).

FIGS. 6A-D: Increased K17 is detected in all grades of urothelial tumors. (a) Papillary urothelial neoplasm of low malignant potential; (b) low-grade papillary urothelial carcinoma, transitioning from adjacent control urothelial mucosa; (c-d) high-grade papillary urothelial carcinoma. Immunohistochemical analysis shows diffuse and robust keratin 17 expression throughout all abnormal urothelial cells (i.e., tumor tissue) (a, b), with high grade urothelial carcinoma exhibiting a more focal K17 expression (c, d).

FIGS. 7A-D: Increased Keratin 17 immunohistochemistry in invasive urothelial carcinoma. (a) Invasive carcinoma found subjacent to non-neoplastic urothelial mucosa; (b) invasive carcinoma in perivesicular soft bladder tissue; (c) K17 expression at invasive front of carcinoma; (d) lamina propria invasion by tumor cells. All tissue samples tested reveal increased keratin 17 expression in tumor cells obtained from subjects with invasive urothelial carcinoma when compared to tissue from healthy patients.

FIGS. 8A-B: Keratin 17 detection using microfluidic detection methods. Samples of (a) HeLa and (b) C33 cells were analyzed. Data shows that there are significantly more K17-labeled cells detected in HeLa (90.4% K17-positive) when compared to C33 (35.1% K17-positive) cells. These data show that detection of K17 can be efficiently achieved using a microfluidic device coupled with K17 immunostaining methods and thus, microfluidic devices, as well as K17 mRNA detection and quantitation methods are suitable means for practicing the present methods.

TABLE 1: Keratin 17 staining in control urothelial mucosa and urothelial bladder cancers. Mean PathSQ scores for control samples (benign) and early stage urothelial bladder cancers (PUNLMP, LG, HG) indicate a significant difference in K17 expression in control bladder tissue samples and urothelial cancer tissue samples (p<0.001).

TABLE 2: immunocytochemical analysis of K17 expression in urine cytology samples. The data compare clinical diagnosis in urine samples from patients with bladder cancer (positive for malignancy) to those that do not have bladder cancer (negative for malignancy or suspicious for malignancy). These data show positive staining for K17 in all samples obtained from subjects having bladder cancer (T3-T7). In contrast, urine samples obtained from non-cancerous patients exhibited no K17 labeling, even where detectable levels of bladder cells are present (N1, N7, N8).

TABLE 3: Detection of K17 expression by immunocytochemical staining of cells isolated from urine. Table 3 shows the results from four independent studies, for a total of 104 patient samples analyzed. Thirty-nine samples from subjects having bladder cancer and 65 samples from benign tissue were analyzed using the present methods. Sensitivity and specificity of K17 detection methods for each study are shown. The results show that the present K17 based diagnostic methods have an average sensitivity of 93% and specificity of 91%.

TABLE 4: Detection limit of ELISA used for detection of Keratin 17 protein in cell-free component of urine. Table 4 shows K17 test results from K17 standards (recombinant K17 protein) with average, standard deviation, and percent coefficient of variation (% CV) tested by ELISA. The cut-off value for a positive signal was determined from negative controls (zero standard/no K17 protein) such that a positive K17 determination is 3-times the standard deviation of the average of the negative control (average of zero standards+ [3×Standard Deviation of zero standards]).

Table 5: Detection of K17 protein in cell-free urine samples from bladder cancer subjects. Table 5 shows data from testing 21 urine samples (6 cancerous, 15 benign/ control). Samples positive for K17 have an average optical density (OD) of at least 0.081 and a % CV less than 20%. The data show that four of the 6 cancers, and none of the benign samples tested positive for K17.

Table 6: Primer set for detection of K17 mRNA by quantitative RT-PCR. Table 6 shows illustrative primer pairs for use in detecting and/or quantitating K17 mRNA by RT-PCR. Suitable primers of the invention, such as those illustrated in Table 6, are designed to generate products that span K17 introns, so that PCR amplification of products of the predicted size occurs only if cDNA generated from K17 mRNA is present in the sample.

DETAILED DESCRIPTION OF THE DISCLOSURE

To date, diagnostic markers (e.g., immunohistochemical markers) of bladder cancers, specifically, early stage bladder cancers (e.g., urothelial cancer) only marginally improve diagnostic accuracy relative to the gold standard of visualization in situ and/or biopsy, e.g. invasive procedures. Conversely, the current disclosure identifies, characterizes and validates a novel biomarker, K17, and provides new methodology with improved diagnostic accuracy, relative to current technology, and is advantageous for use in detecting early stage bladder cancers using immunohistochemical staining of bladder tissue and immuocytological techniques for screening urine cytology samples or nucleic acid-based tests for detecting K17 mRNA. The present disclosure also provides cell-free methods for diagnosing a subject with bladder cancer through the detection of K17 protein or mRNA levels in bladder tissue and urine samples, including cell-free urine samples.

Terminology

The term "peptide" or "protein" as used in the current disclosure refers to a linear series of amino acid residues linked to one another by peptide bonds between the alpha-amino and carboxy groups of adjacent amino acid residues. In one embodiment the protein is keratin 17 (K17).

The term "nucleic acid" as used herein refers to one or more nucleotide bases of any kind, including single- or double-stranded forms. In one aspect of the current disclosure a nucleic acid is DNA and in another aspect the nucleic acid is, such as mRNA. In practicing the methods of the current disclosure, nucleic acid analyzed (e.g., K17 RNA) by the present method is originated from one or more samples.

The terms "cytokeratin 17", "keratin 17", "KRT17" and "K17" as used herein refer to the human keratin, keratin, type II cytoskeletal 4 gene located on chromosome 17, as set forth in accession number NG_008625 or a product thereof, which encodes the type 1 intermediate filament chain keratin 17. Included within the intended meaning of K17 are mRNA transcripts of the keratin 17 cDNA sequence as set forth in accession number NM_000422, and proteins translated therefrom including for example, the keratin, type 1 cytoskeletal protein, 17 as set forth in accession number NP_000413 or homologs thereof.

The phrase "subject", "test subject" or "patient" as used herein refers to any mammal. In one embodiment, the subject is a candidate for bladder cancer diagnosis (e.g., urothelial carcinoma) or an individual with a pre-cancerous lesion, such as urothelial neoplasia. In certain embodiments, the subject has been diagnosed with bladder cancer and the subject is a candidate for treatment thereof. The methods of the current disclosure can be practiced on any mammalian subject that has a risk of developing cancer or has been diagnosed with cancer. Particularly, the methods described herein are most useful when practiced on humans.

A "biological sample," "test sample" or "sample(s)" as used in the instant disclosure can be obtained in any manner known to a skilled artisan. Samples can be derived from any part of a subject, including bladder tissue, urine or a combination thereof. In certain embodiments, the sample is a tissue biopsy, fresh tissue or live tissue extracted from the bladder of subject. In specific embodiments, the sample is a collection of cells from the bladder wall, such as, the transitional epithelium, connective tissue, muscle tissue or fat tissue of the bladder. In other embodiments, the sample is processed prior to use in the disclosed methods. For example, a formalin-fixed, paraffin-embedded tissue sample isolated from a subject are useful in the methods of the current disclosure because formalin fixation and paraffin embedding is beneficial for the histologic preservation and diagnosis of clinical tissue specimens, and formalin-fixed paraffin-embedded tissues are more readily available in large amounts than fresh or frozen tissues. In some embodiments, cells are collected from urine by centrifugation or by filtering, and the collected cells are used for testing. The artisan of skill will take care to ensure that samples are collected, processed, and tested in a manner that prevents avoidable degradation of K17 protein or mRNA, as may vary depending on the test to be employed. In specific embodiments, the sample is a volume of urine obtained from a subject, whereby the urine may or may not have a detectable amount of cells (i.e., the sample may or may not be cell-free). In certain embodiments, the sample is a cell-free urine sample that contains K17 protein or mRNA.

A "control sample", "non-cancerous sample", or "normal sample" as used herein is a sample that does not exhibit elevated K17 and/or exhibits no K17 or reduced K17 levels (where "reduced" is relative to a standard or other known value indicative of cancer). In certain embodiments, a control sample does not contain cancerous cells (e.g., benign tissue components including, but not limited to, normal bladder mucosa, benign bladder mucosal cells, and other non-cancerous cells from the urothelium or transitional epithelium of the bladder). In a specific embodiment, a control or normal sample is a sample from benign tissue that does not exhibit K17 staining or expression. Non-limiting examples of control samples for use in the current disclosure include, non-cancerous tissue extracts, surgical margins extracted from the subject, isolated cells known to have normal or reduced K17 levels, or benign samples or urine obtained from other healthy individuals. In one embodiment, the control sample is human urine from healthy individuals or a formulated urine substitute with no or predetermined amounts of K17 protein or nucleic acid. In one embodiment, the control sample of the present disclosure is benign bladder tissue obtained from the subject in question. In certain other embodiments, the control sample is a urine cytology sample obtained from a healthy subject (i.e., cancer-free patient). In specific embodiments, the control sample is a cell-free volume of urine obtained from a subject, whereby the urine does not have a detectable amount K17 protein or nucleic acid. In other embodiments, the control sample is a cell-free volume of urine Obtained from a subject, whereby the cell-free urine sample has a known amount of detectable K17 protein or nucleic acid.

The term "increase" or "greater" or "elevated" means at least more than the relative amount of an entity identified (such as K17 expression or amounts), measured or analyzed in a control sample. Non-limiting examples include, but are not limited to, a 50% increase over that of a control sample, or at least 30%, 40%, 50%, 60%, 70%, 80%, 90%, 100%, 200%, 300%, 400%, 500%, 1000% or greater increase over that of a negative control sample. In specific embodiments, K17 expression indicative of a subject having bladder cancer includes at least a 1-fold, 1.5-fold, 2-fold, 3-fold, 4-fold, 5-fold, 10-fold, 13-fold, 15-fold, 20-fold, 25-fold, 30-fold or greater, increase relative to the amount of K17 expression exhibited by a control sample. An "increased level of K17 expression" as used in the current disclosure shall mean an increase in the amount of K17 protein or peptide fragments thereof, or RNA present in a cell, organism or sample as compared to a control or normal level of K17 expression or as measured in a reference sample or set by standard. It certain embodiments, the detection of any amount of K17 in a sample is an increase over that of a control. In certain specific embodiments, the increased level of keratin 17 expression that corresponds with bladder cancer is exemplified by the presence of K17 expression at least a 1-fold, 2-fold, 3-fold, 4-fold, 5-fold, 10-fold, 13-fold, 15-fold, 20-fold, 25-fold, 30-fold or greater, increase relative to the amount of K17 expression exhibited by a control sample or set as a standard.

The term "decreased" or "reduction" means at least less than the relative amount of an entity identified, measured or analyzed in a control sample or set by standard.

The phrase "bladder cancer" as used herein includes malignancies in the cells or tissue of the bladder. Bladder cancer includes, for example, malignancies in a cell layer called the urothelium or transitional epithelium, which lines the inside of the ureter, bladder, urethra and parts of the kidneys. In specific instances, bladder cancer includes the presence of cancerous cells in the connective tissue, muscle or adipose layer of the bladder wall. Bladder cancer of the present disclosure can be invasive or non-invasive, papillary or flat cancers of the bladder. "Papillary carcinomas" are exemplified by slender, finger-like projections that grow from the inner surface of the bladder toward the hollow center of the bladder. Papillary tumors that grow toward the center of the bladder without growing into the deeper tissue layers of the bladder wall are noninvasive papillary bladder cancers. In certain embodiments, bladder cancer is papillary urothelial neoplasm of low-malignant potential (PUNLMP). In other instances, bladder cancer is low-grade (slow growing) papillary urothelial carcinoma (LG) or high-grade papillary urothelial carcinoma (HG). In other embodiments, bladder cancer is a transitional urothelial carcinoma. "Flat carcinomas" are bladder cancers that do not grow toward the hollow part of the bladder and primarily replace the transitional epithelium of the bladder wall. In certain embodiments the bladder cancer is a non-invasive flat carcinoma or a flat carcinoma in situ (CIS). In other embodiments, bladder cancer is squamous cell carcinoma, adenocarcinoma, small cell carcinoma or sarcoma of the bladder wall. Bladder cancers detectable using the methods of the instant disclosure can be assigned a "grade", such as low- or high-grade cancers. A "low-grade bladder cancer" is composed of urothelial cells that have the appearance of normal or control bladder urothelial cells and generally have a good or positive prognosis for response to treatment. A "high-grade bladder cancer" is a poorly differentiated or undifferentiated subset of bladder cells that are discernible from normal or control tissue. High-grade bladder cancers are generally more invasive and have a poor prognosis compared to that of a low-grade cancer.

Methods

The present disclosure describes methods for using keratin 17 as a biomarker of bladder cancer. Here, K17 RNA or protein expression was detected by immunohistochemistry, immunocytochemistry, solution or solid phase protein assays (e.g., ELISA, microfluidics, flow cytometry, mass spectrometry) or K17 mRNA was detected or levels of K17 mRNA measured (e.g., by RT-PCR methodology such as Q-RTPCR) in microdissected tissue sections obtained from formalin-fixed paraffin-embedded samples or urine cytology samples for various diagnostic categories (i.e., non-cancerous bladder mucosa, papillary urothelial neoplasm of low-malignant potential (PUNLMP), low-grade papillary urothelial carcinoma (LG), and high-grade papillary urothelial carcinoma (HG) or transitional-urothelial carcinoma). The data show that K17 exhibited about a 30-fold difference in expression between control (benign) and PUNLMP samples; a 15-fold difference in expression between control and LG bladder cancer samples; and a 13-fold difference in K17 expression between control and HG bladder cancer samples. Therefore, the instant disclosure shows that K17 expression can be measured and used as a diagnostic biomarker for the diagnosis of bladder cancer.

One aspect of the present disclosure provides a method for diagnosing a subject with bladder cancer, which includes obtaining a test sample from a subject, and detecting the level of K17 expression in the sample, whereby an increased level of K17 expression in the sample, when compared to that of a control sample identifies the subject as having bladder cancer. In another embodiment, the level of K17 expression is determined by detecting the presence of K17 mRNA in a qualitative or quantitative manner. In a specific embodiment, the level of K17 expression is determined by immunoassay that detects the presence of K17 protein in a qualitative or quantitative manner.

In certain embodiments, K17 expression is determined by detecting binding between K17 and an anti-K17 antibody in a sample. In one embodiment of the present disclosure, a biological sample (i.e., a test sample or control sample) is obtained from the subject in question. A biological sample, which can be used in accordance with the present methods, may be collected by a variety of means known to those of ordinary skill in the art. Non-limiting examples of sample collection techniques for use in the current methods include; fine needle aspiration biopsy, surgical excision biopsy, endoscopic biopsy, and excisional biopsy. In other embodiments, K17 levels can be detected in a sample of urine obtained from a subject that is suspected of having cancer, and the urine sample is subjected to testing to determine the amount of K17 protein or K17 mRNA in the sample. In certain embodiments, the urine samples may be analyzed for the presence of cells or treated so as to collect cells from the urine during the testing. In various other embodiments, however, the samples are processed in a manner that is not dependent on whether cells are present. In specific embodiments, K17 expression can be detected in a urine sample from a bladder cancer patient that is cell free or even from a cell-free portion of voided urine. In other embodiments, the sample is a voided urine sample that contains a detectable amount (number) of cells. By enabling a physician to detect bladder cancer in a voided urine sample with a high degree of sensitivity (few false negatives) and high accuracy (few false positives) at low cost, the present methods provide a benefit over current diagnostics.

In some embodiments, the method includes a control sample, which may be Obtained from non-cancerous tissue or the urine of a subject that does not have cancer. As shown in FIGS. 3A-B and 4C-D a control sample can include voided urine containing a detectable amount of benign urothelial cells. In other embodiments, a control sample is voided urine containing a detectable amount of normal squamous cells, as shown in FIGS. 4A-B. In yet other embodiments, a control sample (non-cancerous) can include bladder mucosal tissue (FIGS. 5A-B and D) or benign bladder mucosal tissue (FIG. 5C), which does not exhibit keratin 17 staining. In other embodiments, the control sample can be a positive control such as a sample that is obtained from a subject known to have bladder cancer that exhibits an increased (strong) level of K17 staining. For example, a positive control sample is voided urine containing a detectable amount of urothelial carcinoma cells, as shown in FIGS. 3C-D that exhibit strong (increased) amounts of keratin 17 expression. In yet other embodiments, a positive control sample (cancerous) includes tissue obtained from subject having papillary urothelial neoplasm of low malignant potential (FIG. 6A), low-grade urothelial carcinoma (FIG. 6B), high-grade papillary urothelial carcinoma (FIGS. 6C-D or invasive urothelial carcinoma (FIGS. 7A-D). Regardless of the type cells or tissue utilized as a positive control sample, such cells must exhibit an increased level of K17 expression. Moreover, and particularly in high throughput embodiments of the present disclosure, present methods will be deployed with automated equipment and computer controlled analytics such that there will either be no control, or the control will be a formulated liquid or material or even a user or instrument maker set pre-determined value.

While bladder cancer may result in the presence of cancer cells in the urine, it is an unexpected aspect of the present disclosure that the amount of K17 in cell-free urine samples from cancer patients is sufficient to enable such samples to be distinguished from normal (non-cancerous) samples. Further, since quality control and cell collection steps of cell-based assays are expensive, implementation of this embodiment of the present disclosure will significantly reduce the costs associated with current invasive tests. Thus, in some embodiments, the sample is fluid, urine, that does not include a detectable amount of cells, i.e., a cell-free sample. For these specific embodiments, the control sample can be a cell-free urine sample that contains a previously determined (known) amount of K17 protein or RNA, which amount may be none or an amount below the limits of detection. In some embodiments, the cell-free urine sample contains a detectable amount of K17 protein or RNA (e.g. a sample from a bladder cancer patient or a control sample). In other embodiments, the cell-free urine sample contains no detectable amount of K17 protein or RNA (negative control sample or sample from a subject that does not have bladder cancer). In embodiments whereby the methods deployed analyze keratin 17 expression in a cell-free portion of voided urine, a control sample can be a fluid sample (e.g., urine) that includes a known amount of K17 protein (which can be zero, for a negative control) or that of normal bladder cells from a healthy patient. In other embodiments, a control sample can be a positive control, such as a fluid sample (e.g., urine) that includes a known amount of K17 protein from a subject known to have bladder cancer or in an amount that would be higher than that expected if the subject did not have bladder cancer.

In certain embodiments, the sample obtained from a subject is used directly without any preliminary treatments or processing, such as formalin-fixation, flash freezing, or paraffin-embedding. In a specific embodiment, a biological sample can be obtained from a subject and processed by formalin treatment and embedding the formalin-fixed sample in paraffin. In certain embodiments, a sample may be stored prior to use. As such, the present diagnostic methods can be applied using multiple preparation methods including preparation for use in immunohistochemistry staining instruments (e.g., autostainers) such as Autostainer Link (Dako), Discovery XT and BenchMark XT (Ventana Medical Systems, Inc.), Leica® ST5010 Autostainer XL, Leica® Multistainer ST5020 (Leica Biosystems Nussioch GmbH), Autostainer Link 48 (Agilant), and Lab Vision™ Autostainer 360-2D, Lab Vision™ Autostainer 480s (Thermo Fisher Scientific™).

In some embodiments, the sample used in the present methods is urine obtained from a subject. In certain embodiments, the urine sample includes a detectable amount of cells that can be tested and analyzed for K17 expression. In some embodiments, the cells are from the bladder wall of the subject. In specific embodiments, the sample contains a detectable amount of cells that express K17.

After a suitable sample is obtained, the level of K17 expression in the sample can be determined using various techniques known by those of ordinary skill in the art. In certain embodiments of the current disclosure K17 expression levels may be measured by: immunohistochemistry (MC), qRT-PCR, northern blotting, western blotting, enzyme-linked immunosorbent assay (ELISA), microarray analysis, or mass spectrometry. In specific embodiments, K17 is detected by a solution phase protein assay (e.g., ELISA, microfluidics, flow cytometry). In a specific embodiment, K17 expression is determined by immunohistochemical staining of a urine sample that includes a detectable amount of bladder cells. In other embodiments, K17 expression is determined by the detection of fluorescently labeled cells by flow cytometry or microfluidic based detection methods. In specific embodiments, the fluorescently labeled cells express keratin 17. In some embodiments, the level of K17 expression is determined by detecting the presence of K17 mRNA or protein in a sample. In some embodiments, any amount of K17 mRNA or protein detected in the sample is correlated with a diagnosis of bladder cancer. In other embodiments, the amount of K17 protein or mRNA in a sample must exceed the amount present in a control sample.

Any type of antibody can be used against the K17 antigen including, but not limited to, mouse monoclonal-[E3] anti-human K17 antibody, polyclonal antibodies against human K17, a monoclonal antibody or polyclonal antibody against a mammalian K17 protein domain or epitope thereof. Also applicable are chimeric, single chain, Fc, Fab, Fab', and Fab2 fragments of immunoglobulin molecule, and a Fab expression library against K17 protein. The referenced antibodies include all classes, subclasses, and type and immunoglobulins, and also include hapten molecules (e.g., nucleic acids, polymers) that bind to K17 protein.

In certain embodiments, after incubation with the primary antibody, samples are processed by an indirect avidin-biotin-based immunoperoxidase method using biotinylated secondary antibodies, developed, and counter-stained with hematoxylin. Slides can then be analyzed for K17 expression.

In certain embodiments, keratin expression is quantified by the PathSQ method, a manual semi-quantitative scoring system, which quantifies the percentage of strongly stained cells, blinded to corresponding clinical data. In yet another embodiment, slides can be scored by the National Institutes of Health ImageJ 1.46, Java-based image processor software using the DAB-Hematoxylin (DAB-H) color deconvolution plugin. See Schneider Calif., et al., *Nat methods*. (2012) 9:671-5, the entire contents of which is expressly incorporated herein by reference.

As shown in Table 1 of the instant application, immunohistochemical analysis of K17 is conducted on formalin-fixed, paraffin-embedded samples. Here, normal bladder mucosa (control sample), PUNLMP, LG papillary urothelial carcinoma, and HG papillary urothelial carcinoma test samples from hematoxylin and eosin stained tissue sections were dissected by laser capture microscopy and bladder wall cells are collected from each diagnostic category. Formalin-fixed, paraffin-embedded tissue samples are then processed using an indirect immunoperoxidase method. Specifically, samples are then incubated with protease cocktails to facilitate the reverse of protein cross-linking. After incubation, at elevated temperature (greater than 50° C.), tissue samples are deparaffinized and rehydrated. Antigen retrieval is then performed in citrate buffer in a decloaking chamber. Endogenous peroxidase is blocked, and samples are labeled by incubation with a K17-specific antibody. After primary antibody incubation, secondary antibodies are added, and the samples are developed and counterstained with hematoxylin. Negative controls from control tissue samples are processed using an equivalent method.

In a specific embodiment, immunohistochemical stains for K17 in negative control samples (benign) and bladder cancer samples (PUNLMP, LG, HG, transitional-urothelial carcinoma) are scored by PathSQ, a manual semiquantitative scoring system, which quantifies the percentage of strongly stained [cancer] cells, blinded to corresponding clinical data, and the fold increase over K17 expression levels in a control sample is calculated. See FIG. 3C-D. For tissue biopsy, the PathSQ score must be at least 5%. In other embodiments, the PathSQ score is between 5% and 99%, 10% and 90%, 20% and 80%, 30% and 70%, or 40% and 60%. In other embodiments, one of ordinary skill in the art will be able to determine the PathSQ score of a sample that corresponds to the presence of cancer.

In a specific embodiment, K17 protein detection is carried out via tissue microarray. For example, tissue containing normal bladder mucosa, PUNLMP, LG, HG or transitional-urothelial bladder cancer cells can be obtained from paraffin blocks and placed into tissue microarray blocks. In certain embodiments, other sources of bladder cancer cells can be used as test samples. In particular, urine samples that contain bladder wall cells or urine samples that contain no cells but do contain proteins and/or snRNA derived from bladder wall cells are ideal test samples. Control samples for use in determining the fold increase in K17 in a sample over that of a control sample can be obtained from, for example, commercial tissue microarray samples, such as those obtained from HISTO-Array™. Tissue microarray slides for use in the current methods can then be processed, i.e., deparaffinized in xylene and rehydrated using an alcohol. In certain embodiments, samples can be further processed by: incubation with a citrate buffer, applying hydrogen peroxide to block endogenous peroxidase, or by treating the sample with serum to block non-specific binding (e.g., bovine, human, donkey or horse serum). The samples are further labeled by incubation with primary antibodies against K17.

In some embodiments and as shown in FIGS. 2, 3A-D through 5A-D and Tables 2 and 3 of the present disclosure, K17 expression can be determined from a urine cytology sample by immunocytochemical analysis of a detectable amount of cells. Here, voided urine samples are collected from a subject in question and bladder cells are isolated from the sample using techniques known by those of ordinary skill in the art such as centrifugation or filtering. Isolated bladder cells are then affixed to slides, labeled for K17 using routine immunocytochemical methods, counterstained for hematoxylin and scored using microscopy for K17 expression in both test and control urine samples.

For example, FIGS. 2 and 3A and B show keratin 17 staining for control samples obtained from cells isolated from voided urine obtained from a healthy (non-cancerous)

subject. These cells show sparse ("control levels") of K17 staining. In comparison, FIGS. 3C-D show strong keratin 17 staining in urothelial cells obtained from the voided urine of a subject having bladder cancer (urothelial carcinoma). Additional examples of negative control levels of keratin 17 expression are in FIGS. 4A-D and 5A-D, which depict healthy squamous (FIG. 4A-B) and healthy, non-cancerous urothelial cells (FIGS. 4C-D), as well as non-cancerous bladder mucosa (FIGS. 5A,B & D) and benign bladder mucosal tissue (FIG. 5C).

In yet another embodiment, K17 mRNA expression can be determined using reverse transcriptase PCR (RT-PCR) in a qualitative format and by quantitative-RT-PCR. More specifically, total RNA can be extracted from a sample using a Trizol reagent. Reverse transcriptase-PCR can then be performed using methods know by one of ordinary skill in the art. For example, 1 µg of RNA can be used as a template for cDNA synthesis, and cDNA templates can then be mixed with gene-specific primers (i.e., forward, 5'-3' primer sequence and reverse 3'-5' sequence) for K17 mRNA. Examples of K17 primers are shown in Table 6. Probe sequences for detection can also be added (e.g., TaqMan™ from Applied Biosystems and SYBR® Green from Thermo Fisher Scientific systems are known in the art and useful for this purpose). Real-time quantitative PCR can then be carried out on each sample and the data obtained can be normalized to control levels K17 mRNA expression levels as set forth in a control or normal sample (i.e., benign bladder mucosa). See, for example, Schmittgen, and Livak, *Nature protocols* (2008) 3: 1101-1108. Other nucleic acid detection technologies including, but not limited to, nucleic acid sequence based amplification (NASBA), loop mediated isothermal amplification (LAMP), strand displacement amplification (SDA), multiple displacement amplification (MDA), rolling circle amplification, ligase chain reaction (LCR), helicase dependent amplification, ramification amplification, or branched DNA can also be used to detect K17 mRNA or otherwise quantify K17 mRNA expression.

In other embodiments, where K17 protein detected, the methods of the present disclosure can be deployed using enzyme-linked immunosorbent assays (ELISA) to determine K17 expression in a sample. Additionally, mass spectrometry and lateral flow protein detection assays can be used to detect and quantitate K17 expression levels in a sample. For example, as shown in Tables 4 and 5, a sample such as voided urine can be prepared by centrifugation to isolate bladder cells present in the sample. In certain embodiments, such as cell-free based methods of diagnosis, the cell-free portion of the test sample can be isolated and examined for K17 protein expression using an ELISA system. For a cell-free ELISA based detection method, a microtiter plate is coated with a coating solution including an anti-keratin 17 antibody such as K17 E3 monoclonal antibody and incubated. The microtiter plate can then be blocked to prevent non-specific binding of K17 protein. Next, a predetermined amount of a test sample is added to each well of the microtiter plate and incubated. A detection solution containing K17 antibodies labeled with a detectable marker such as a peroxidase (e.g., 2D10 monoclonal antibody labeled with peroxidase) is then added to each well and incubated. In certain embodiments, the wells can be washed prior to adding a detection substrate that is capable of reacting with the detectable marker to emit a signal. After incubation, each plate is read by emitting a detectable wavelength of light such as 450 nm, and the amount of keratin 17 protein in the sample is determined. In certain embodiments, control samples, e.g., calibrators are run in serial and the amount of K17 protein in the test sample can then be compared to that of the controls to determine whether a subject has bladder cancer by inference from the amount of K17 protein detected, with a diagnosis of cancer correlating with detected amounts exceeding control amounts or standards.

In an embodiment, the methods of the present disclosure can be deployed using flow cytometry. In one embodiment of the present disclosure, a microfluidic flow cytometry system is provided that can detect labeled cells using detectable tags to detect and/or quantitate K17 protein or mRNA, e.g., determine K17 expression or expression levels, in a sample. As exemplified in FIGS. 8A-B, a cell-containing sample such as voided urine or a bladder tissue sample is obtained and prepared. In certain embodiments, the urine sample is processed or prepared by fixing the cells in methanol and isolating the fixed cells by centrifugation. In some embodiments, cells are suspended in phosphate buffer solution (PBS) and contacted with an anti-keratin 17 antibody (such as K17 E3 monoclonal antibody (Abeam) and incubated to permit binding to K17 present in the sample. The sample can then be washed to limit non-specific binding. The sample is then contacted with a secondary antibody that includes a detectable marker such as phycoerythrin and incubated to permit specific binding to labeled K17 in the sample. The sample is then suspended in fluid and aliquoted into a cartridge. The cartridge can then be read in a microfluidic detection system such as Moxi Go system (Orflo Technologies Inc.) to determine the amount of K17 present in the sample. In certain embodiments, control samples, e.g., reference samples, are run in the same manner and the amount of K17 protein in the test sample is compared to that of the controls to determine whether a subject has bladder cancer. In other embodiments, any amount of K17 detected in a test sample above a pre-set standard amount is correlated with increased K17 expression levels and thus the diagnosis of bladder cancer.

In one embodiment of the current methodology of the instant disclosure, the amount of K17 (protein or mRNA) in a sample is compared to either a control amount of K17 present in a normal bladder cell or a non-cancerous cell (or tissue or urine sample or cell sample derived from either), or to the amount of K17 (protein or mRNA) in a control sample. The comparison can be done by any method known to a skilled artisan for detecting and quantitating a protein or mRNA. In a specific embodiment, the amount of K17 expression indicative of a subject having bladder cancer includes, but is not limited to, a 30%, 40% 50%, 60%, 70%, 80%, 90%, 100%, 200%, 300%, 500%, 1000% or greater increase over that of a control sample.

In other embodiments, K17 expression indicative of a subject having bladder cancer includes at least a 1-fold, 1.5-fold, 2-fold, 3-fold, 4-fold, 5-fold, 10-fold, 13-fold, 15-fold, 20-fold, 25-fold, 30-fold or greater, increase relative to the amount of K17 expression exhibited by a control sample. In certain specific embodiments, the K17 expression as measured by PathSQ that corresponds with early stage bladder cancer in a subject is exemplified by K17 staining in a sample that exhibits an increase in K17 expression from 10-fold to 60-fold over that of a control (benign) sample. In other embodiments, early stage bladder cancer in a subject is exemplified by K17 staining in a test sample that exhibits an increase in K17 expression from 13-fold to 30-fold over that of the control sample. In a specific embodiment, early stage bladder cancer in a subject is exemplified by K17 staining in a test sample that exhibits an increase in K17 expression of about 13-fold, about 15-fold or about 30-fold over that of the control sample. In preferred embodiments of the present disclosure, a test sample exhibiting K17 expression having a PathSQ score of greater than 30 indicates that the subject has a lesion that is equal to or greater than papillary urothelial neoplasm of low-malignant potential (PUNLMP). In embodiments where the test sample exhibits K17 expression having a PathSQ score of between 30 and 35, the subject has low-grade papillary urothelial carcinoma (LG). In embodiments where the test sample exhibits K17 expression having a PathSQ score of 29 or less the subject has high-grade papillary urothelial carcinoma (HG). In a specific embodiment where the test sample exhibits K17 expression having a PathSQ score of between 12 and 46 the subject has bladder cancer.

In yet other embodiments, K17 expression indicative of a subject having bladder cancer includes an optical density reading of a test sample of at least 0.065, at least 0.070, at least 0.075, at least 0.080, at least 0.081, at least 0.085, at least 0.090 or higher. In certain embodiments, K17 expression indicative of a subject having bladder cancer includes an optical density reading of a test sample of between 0.065 and 0.2, between 0.065 and 0.1, 0.075 and 0.2, 0.075 and 0.1, 0.08 and 0.2, 0.08 and 0.15, 0.08 and 0.1, 0.08 and 0.09, inclusive. In specific embodiments, K17 expression indicative of a subject having bladder cancer includes an optical density reading of a test sample of 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30 or greater.

The present methods can also be used to diagnose the presence of other K17 mediated diseases. As such, the methods of the present disclosure are not intended to be limited by the foregoing description or examples that follow.

EXAMPLES

Example 1. Materials and Methods

The studies carried out included the analysis of 84 formalin-fixed paraffin-embedded surgical tissue blocks (Table 1). All surgical tissue blocks were obtained from subjects (patients) suspicious for having bladder cancer. These study cases comprised the following diagnostic categories: benign urothelium, (n=12), papillary urothelial neoplasm of low malignant potential (PUNLMP) (n=9), low-grade papillary urothelial carcinoma. (n=23), high-grade papillary urothelial carcinoma (n=14), transitional/urothelial carcinoma (n=26). In certain cases, a tissue block was selected following histologic review by a pathologist (DCM) of hematoxylin-eosin stained sections from either transurethral resection (TURBT), bladder biopsy or cystectomy specimens to confirm that diagnostic tissue as originally reported, was adequately represented in the remaining tissue blocks. Cases that had insufficient residual tissue or for which diagnostic tissue could not be preserved for future clinical use were not included in the study. Bladder cancer was classified by: (i) clinical stage according to Edge S B and Compton C C. *Annals of surgical oncology*. (2010) 17:1471-4, the entire content of which is incorporated herein by reference; and (ii) tumor grade (Table 1).

Immunohistochemistry. Immunohistochemical analysis was performed by an indirect immunoperoxidase method, as previously described in L. Escobar-Hoyos et al., *Cancer Res*. 2015 Sep. 1; 75(17):3650-62), which is expressly incorporated herein, it its entirety, by reference. Briefly, after incubation at 60° C., tissue sections were deparaffinized in xylene and rehydrated in alcohol. Antigen retrieval was performed in citrate buffer at 120° C. for 10 minutes in a decloaking chamber. Endogenous peroxidase was blocked by 3% hydrogen peroxide, and sections were labeled overnight at 4° C. with mouse monoclonal-[E3] anti-human K17 antibody (Abcam®) or and Ki-67 (clone MIB-1, 1:100 dilution, DAKO, Carpentaria, Calif., USA) for bladder cancers. Other antibodies for use in the present methods, which bind and label K17 including Anti-Cytokeratin 17 antibody [EP1623]-Cytoskeleton Marker ab109725 (Abcani®), Keratin 17 (D73C7) Rabbit mAb (Cell Signaling Technology®), Guinea pig Polyclonal (IgG) to Human K17 LS-C22650 (LifeSpan BioSciences, Inc.), Rabbit polyclonal antibody to Keratin 17 orb22505 (Biorhyt). After primary antibody application, biotinylated horse secondary antibodies (R.T.U. Vectastain ABC kit; Vector Laboratories) were added to the sample. Development was carried out with 3,3'-diaminobenzidine (DAB; Dako), and counterstained with hematoxylin. Negative controls were performed on all runs using an equivalent concentration of a subclass-matched immunoglobulin. Immunohistochemical stains for K17 in bladder cancer were scored by PathSQ, a manual semiquantitative scoring system, which quantifies the percentage of strongly stained tumor cells, blinded to corresponding clinical data. PathSQ is based on the proportion of tumor cells with strong (i.e., 2+) staining. Ki-67 staining was scored as a percentage of tumor cells with positive nuclear staining.

K17 Detection by Microfluidics.

In addition to immunostaining of urine cytology samples, K17 positive cells in urine could be detected by application of flow cytometry or a microfluidic system that can detect labeled cells using fluorescent tags. One example of such system is Moxi Go system (Orflo Technologies Inc.) that utilizes a disposable microfluidic cartridge and a reader that can count the number of cells based on size (Coulter method) and fluorescence signal (Phycoerythrin). Detection of K17-positive cells using a Moxi Go microfluidic device (Orflo Technologies Inc.) was tested using K17-positive (Hela) and K17-negative (C33) cells as controls. Cells (approximately $1 \times 10^5$ cells) were fixed in 70% methanol for 1 hour, pelleted by centrifugation at 1000 g for 5 minutes, then washed with 1 mL 1×PBS. Cells were then pelleted and resuspended in 100 µL phosphate buffer solution (PBS). Next, 50 µL of cells were mixed with 50 µL of Keratin 17 antibody (E3, Abeam), and incubate at room temp for 2 hours. Cells were then pelleted and washed once with 1 mL PBS, and pelleted again. Pelleted cells were then resuspended in 50 µL anti-mouse antibody labeled with phycoerythrin (PE) (1:100 dilution in PBS, Abeam), and incubate at room temp for 30 min. Cells were washed twice with 1 mL PBS, and finally resuspended in 500 µL PBS. The labeled cells were read on a Moxi Go microfluidic instrument by adding 75 µL of each of the samples onto the microfluidic cartridge and reading it on the instrument.

Detection of L17 Using ELISA.

Keratin 17 protein, in the cell-free component of urine was tested by ELISA on voided urine samples. Voided urine was centrifuged at 1000 g for 5 mins to pellet the cells. After the centrifugation, the liquid cell-free portion of the urine was decanted and used for testing in K17 ELISA. For ELISA, high-binding microtiter plate was coated with 100 µL of K17 coating solution per well using K17 E3 monoclonal antibody at concentration of 2 µg/mL in 1×PBS (Nordic MUBio, Systeren, Netherlands), and incubate at 4° C. overnight. Each plate was then blocked with 200 µL of blocking buffer (SuperBlock PBS Blocking Solution, ThermoFisher Scientific) per well, and incubated at room temperature (RT) for 1 hour.

Samples were the tested by adding 100 µL of urine sample to each well with 100 µL of assay Buffer (10% Calf Serum in 1×PBS) in duplicate and incubated at RT for 1 hour. The samples were run with K17 calibrators (Keratin 17 recombinant protein, Abcam) starting from 1 µg/mL in 3-fold serial dilution on the same plate. Each plate was then washed 4-times with 400 µL of wash buffer (0.05% Tween-20 in 1×PBS), and 100 µL of detection antibody solution containing K17 2D10 monoclonal antibody labeled with peroxidase (K17 2D10 monoclonal antibody-HRP, US Biologicals) at a final concentration of 1 µg/mL in assay buffer and samples were incubated at RT for 1 hour. Cells were then washed and 100 µL of TMB substrate (Pierce) was added to each well, and samples were incubated at RT in dark for 20 minutes. The reaction was then stopped using 100 µL of stop solution (VWR) and the plate was read at 450 nm.

Scoring of Keratin Protein Expression.

Slides were scored by the National Institutes of Health ImageJ 1.46 (see Schneider C A, et al., *Nat methods*. (2012) 9:671-5, the contents of which is incorporated herein by reference) Java-based image processor software using the DAB-Hematoxylin (DAB-H) color deconvolution plugin (see Ruifrok A C, Johnston D A. *Anal Quant Cytol Histol.* (2001) 23:291-9, the entire contents of which is incorporated herein by reference) and by a manual semi-quantitative scoring system, which quantifies the percentage of strong-positively stained cells blinded to corresponding clinical data (PathSQ). In certain embodiments, the unit of measurement for immunohistochemical analysis was the core PathSQ score and the average PathSQ score of all core scores. The score differences between diagnostic categories were determined by Kruskal-Wallis or Wilcoxon rank-sum test (not shown). Receiver operating curves and the area under the curve were calculated to evaluate biomarker potential to discriminate different diagnostic categories based on logistic regression models. The optimal cut-off value from receiver operating curves was determined using Youden's index, See Youden W J. *Cancer*. (1950) 3:32-5, the contents of which are incorporated herein by reference.

Example 2: Keratin 17 Detection in Immunohistochemical Stained Cells as Diagnostic Method for Bladder Cancer To determine the diagnostic values of K17 in one or more diagnostic categories of early stage bladder cancer, immunohistochemical staining (Table 1) was performed for K17 on tissue of archived bladder cancer patient tissue samples from four diagnostic categories: benign bladder mucosa (benign), papillary urothelial neoplasia of low malignant potential (PUNLMP), low-grade papillary urothelial carcinoma (LG), high grade papillary urothelial carcinoma (HG) and urothelial carcinoma.

K17 staining was only faintly detectable (mean PathSQ score of 2.08) in benign bladder mucosa, but was highly expressed in all diagnostic categories of bladder cancer examined. For example, Table 1 shows that mean PathSQ scores ranged from 12.3831954 to 45.1781993 for HG and PUNLMP samples, respectively (Table 1), whereas the mean PathSQ score of control (non-cancerous) samples was approximately 2. Further, FIGS. 3A-D and a comparison of the control samples shown in FIGS. 4A-D and 5A-D to cancerous samples stained in FIGS. 6A-D through 7A-D reveal that strong (increased) keratin 17 stating is present only in samples obtained from subjects having bladder cancer. Taken together, these results show that K17 is a strong diagnostic marker for bladder cancer, such as urothelial carcinoma of the bladder (p<0.001).

Among the urine samples tested that contained bladder wall cells, K17 staining was detected in 5/5 samples that had been diagnosed as suspicious or positive for bladder cancer. See Table 2. As shown in Table 2, K17 expression was absent in cases that were negative for malignancy. These data clearly show positive staining for K17 in all samples obtained from a subject having bladder cancer (T3-T7). In contrast, urine samples obtained from non-cancerous patients exhibited no K17 labeling, where detectable levels of bladder cells are present (N1, N7, N8). These results provide experimental support that K17 detection is a diagnostic marker of bladder cancer.

The immunohistochemistry results obtained using bladder tissue samples provided support for the hypothesis that K17 detection could be a sensitive and specific marker to improve accuracy for the diagnosis of bladder cancer in urine cytology specimens. As shown in, Table 3 of the present disclosure K17 detection provides sensitivity and specificity as a diagnostic marker for bladder cancer. For example, as a result of multiple studies conducted on voided urine samples containing bladder cells (FIG. 2), K17 shows a sensitivity (number of true K17 positive samples/number of detected K17 positive samples) of 93% and specificity (number of true K17 negative samples/number of detected K17 negative samples) of 91%. For Study 2, most false-positive samples were performed with direct spotting of samples, whereas Study 3 was performed using ThinPrep sample preparation methods. Taken together, the data provided shows that detection of K17 by immunostaining of bladder cells in urine samples can detect the presence of bladder cancer in a subject with high sensitivity and specificity.

Example 3: Keratin 17 Detection in Cells Through Automated Device Based Detection Methods In addition to immunostaining of urine cytology samples, K17 positive cells in urine cytology samples is detectable by flow cytometry and microfluidic device systems capable of detecting fluorescently tagged proteins. Here, labeled cancer cells known to be positive for K17 (HeLa, FIG. 8A) and K17-negative, control cells (C33, FIG. 8B) were isolated, fluorescently labeled with K17 antibodies and K17 expression was analyzed on a microfluidic detection device, as set forth above. As seen in FIGS. 8A-8B, there are significantly more K17-labeled cells in Hela (90.4% K17-positive) compared to control, C33 cells (35.1% K17-positive). Taken together, these data show that detection of K17 positive cells can be efficiently achieved using a microfluidic device coupled with K17 immunostaining.

Example 4: Cell-Free K17 Based Diagnostic Methods

As shown in Tables 4 and 5 test samples composed of voided urine that are devoid of bladder cells can be analyzed for K17 protein expression to determine whether a subject has bladder cancer. For example, Table 4 shows results obtained using an ELISA based K17 detection method. Here, control samples (i.e., calibrators) having a known amount of K17 protein were analyzed to determine the sensitive of the ELISA system testing in cell-free samples. A cut-off value for increased K17 protein expression was determined from the negative controls (zero calibrator) where the detectable signal was 3-times the standard deviation of the blanks from the average of the negative control. For example the following formula was used: Average of negative control ELISA readings+[3-times the standard deviation of the negative controls]. Based on the data, the limit of sensitivity of the ELISA is approximately 1 ng/mL of K17 protein.

Table 5 shows the data from 21 cell-free urine samples (6 cancerous, 15 benign, positive samples in bold) obtained from subjects. Here, each of the 21 test samples were run on an ELISA system and K17 expression in the cell-free portion of voided urine was detected in each sample and compared to control levels in Table 4. A test sample exhibiting an average optical density (OD) reading of 0.081 or higher with % CV less than 20% correlated well with the presence of bladder cancer in a subject. For example, 67% of cancer samples (4 of 6 samples) exhibited an OD reading of 0.081 or greater, while none of the non-cancerous control samples showed a detectable of level K17 over 0.078 OD. As this was a model experiment and not an actual patient test, the lack of detectable K17 signal in two of the cancer samples is believed to be due to an uncontrolled test factor, such as the time of the sample collection, as a first morning void will have higher level of accumulated K17 protein than voids at other times of day, or due to sample handling Taken together, these data demonstrate that the present disclosure provides a method by which measurement of detectable levels of K17 protein in cell-free urine samples can be used to detect the presence of bladder cancer (e.g. diagnose bladder cancer) in a subject using ELBA or other protein based detection platforms such as mass spectrometry or lateral flow instrumentation.

TABLE 1

Keratin 17 staining in control urothelial mucosa and urothelial bladder cancers.

| Sample | Number (N) | K17 Expression (Mean) | Fold increase in K17 Expression Over Benign |
|---|---|---|---|
| Benign | 12 | 2.08 | |
| PUNLMP | 9 | 65.56 | 31.5 fold |
| LG | 23 | 34.57 | 16.6-fold |
| HG | 14 | 29.36 | 14.1-fold |
| Transitional/urothelial Carcinoma | 26 | 49.23 | 23.7-fold |

TABLE 2

Immunocytochemical analysis of K17 expression in urine samples.

| Decoded Subject ID Number | Cytologic Diagnosis | K17 Expression |
|---|---|---|
| T1 | Suspicious for Malignancy | acellular |
| T2 | Suspicious for Malignancy | acellular |
| T3 | Positive for Malignancy | moderately cellular, degenerative changes, strong positive |
| T4 | Positive for Malignancy | moderately cellular, faint positive |
| T5 | Positive for Malignancy | highly cellular, strong positive |
| T6 | Positive for Malignancy | moderately cellular, faint positive |
| T7 | Positive for Malignancy | highly cellular, strong positive |
| T8 | Suspicious for Malignancy | acellular |
| N1 | Negative for malignancy | sparse cellularity, proteinaceous debris, negative |
| N2 | Negative for malignancy | acellular |
| N3 | Rare reactive and degenerated urothelial cells present. | acellular |
| N4 | Negative for malignancy | acellular |
| N5 | Negative for malignancy. | acellular |
| N6 | Negative for malignancy | acellular |
| N7 | Negative for malignancy | sparse cellularity, negative |
| N8 | Negative for malignancy | moderately cellular, negative |

TABLE 3

Detection of K17 expression by immunostaining of cells isolated from urine.

| | Study 1 | Study 2 | Study 3 | Study 4 | Total |
|---|---|---|---|---|---|
| Malignant | 3 | 10 | 5 | 21 | 39 |
| Benign | 5 | 20 | 18 | 22 | 65 |
| Total | 8 | 30 | 23 | 43 | 104 |
| True Pos | 5 | 9 | 5 | 17 | |
| False Neg | 0 | 1 | 0 | 4 | |
| True Neg | 3 | 14 | 18 | 21 | |
| False Pos | 0 | 6 | 0 | 1 | Avg. |
| Sensitivity | 100% | 90% | 100% | 81% | 93% |
| Specificity | 100% | 70% | 100% | 95% | 91% |

TABLE 4

Detection limit of ELISA used for detection of Keratin 17 protein in cell-free component of urine.

| Calibrator (ng/mL) | OD-1 | OD-2 | Avg. | STDEV | % CV |
|---|---|---|---|---|---|
| 1000 | 3.555 | 3.624 | 3.590 | 0.049 | 1% |
| 333.3 | 3.578 | 3.604 | 3.591 | 0.018 | 1% |
| 111.1 | 2.469 | 2.289 | 2.379 | 0.127 | 5% |
| 37.0 | 0.844 | 0.832 | 0.838 | 0.008 | 1% |
| 12.3 | 0.323 | 0.318 | 0.321 | 0.004 | 1% |
| 4.1 | 0.142 | 0.14 | 0.141 | 0.001 | 1% |
| 1.4 | 0.087 | 0.081 | 0.084 | 0.004 | 5% |
| 0 | 0.067 | 0.058 | 0.063 | 0.006 | 10% |

Cutoff = 0.082

TABLE 5

Detection of K17 proteins in the cell-free portion of urine samples to detect the presence of bladder cancer in subjects.

| Samples | Diagnosis | OD-1 | OD-2 | Avg. | STDEV | % CV |
|---|---|---|---|---|---|---|
| N281-1 | Benign | 0.069 | 0.070 | 0.070 | 0.001 | 1% |
| N281-2 | Benign | 0.056 | 0.053 | 0.055 | 0.002 | 4% |
| CT7699 | Benign | 0.055 | 0.054 | 0.055 | 0.001 | 1% |
| CT7304 | Benign | 0.056 | 0.054 | 0.055 | 0.001 | 3% |
| GC 19-1 | Cancer | 0.064 | 0.066 | 0.065 | 0.001 | 2% |
| GN19-1 | Benign | 0.059 | 0.059 | 0.059 | 0.000 | 0% |
| GN19-2 | Benign | 0.063 | 0.06 | 0.062 | 0.002 | 3% |
| GN19-3 | Benign | 0.111 | 0.078 | 0.095 | 0.020 | 25% |
| GC24-1 | Cancer | 0.090 | 0.093 | 0.092 | 0.002 | 2% |
| GN24-1 | Benign | 0.056 | 0.055 | 0.056 | 0.001 | 1% |
| GN24-2 | Benign | 0.062 | 0.061 | 0.062 | 0.001 | 1% |
| GN24-3 | Benign | 0.078 | 0.078 | 0.078 | 0.000 | 0% |
| GN24-4 | Benign | 0.056 | 0.056 | 0.056 | 0.000 | 0% |
| G6117-1 | Benign | 0.051 | 0.055 | 0.053 | 0.003 | 5% |
| G6117-2 | Cancer | 0.072 | 0.09 | 0.081 | 0.013 | 16% |
| G6717-1 | Cancer | 0.092 | 0.09 | 0.091 | 0.001 | 2% |
| G6717-2 | Benign | 0.075 | 0.078 | 0.077 | 0.002 | 3% |
| G6817-1 | Cancer | 0.050 | 0.059 | 0.055 | 0.006 | 12% |
| G6817-2 | Benign | 0.058 | 0.062 | 0.060 | 0.003 | 5% |
| G629-1 | Cancer | 0.088 | 0.095 | 0.092 | 0.005 | 5% |
| G629-2 | Benign | 0.067 | 0.06 | 0.064 | 0.005 | 8% |

TABLE 6

Primer set for detection of K17 mRNA by quantitative RT-PCR.

| Pair | Forward Primer (5'-3') | Reverse Primer (5'-3') | Product length (bp) |
|---|---|---|---|
| 1 | SEQ ID NO: 1 CAGTCCCAGCTCAGCATGAA | SEQ ID NO: 2 CCACAATGGTACGCACCTGA | 295 |
| 2 | SEQ ID NO: 3 AGAACCTCAATGACCGCCTG | SEQ ID NO: 4 TCCACAATGGTACGCACCTG | 973 |
| 3 | SEQ ID NO: 5 CAAGGATGCCGAGGATTGGT | SEQ ID NO: 6 ACAATGGTACGCACCTGACG | 432 |
| 4 | SEQ ID NO: 7 TCCTCAACGAGATGCGTGAC | SEQ ID NO: 8 CACAATGGTACGCACCTGAC | 482 |
| 5 | SEQ ID NO: 9 GGATGCCGAGGATTGGTTCT | SEQ ID NO: 10 AATGGTACGCACCTGACGG | 427 |
| 6 | SEQ ID NO: 11 GCAGAGAAGAACCGCAAGGA | SEQ ID NO: 12 ACCTCTTCCACAATGGTACGC | 455 |
| 7 | SEQ ID NO: 13 GCTCAGCATGAAGCATCCC | SEQ ID NO: 14 CCTCTTCCACAATGGTACGC | 293 |
| 8 | SEQ ID NO: 15 CCATGCAGGCCTTGGAGATA | SEQ ID NO: 16 GTGGTCACCGGTTCTTTCTTG | 298 |
| 9 | SEQ ID NO: 17 CCGTCAGGTGCGTACCATT | SEQ ID NO: 18 TTGTCATCAGGCAAGGAAGCA | 216 |
| 10 | SEQ ID NO: 19 GGTGAAGATCCGTGACTGGT | SEQ ID NO: 20 TTCCACAATGGTACGCACCTG | 901 |

What is claimed is:

1. A method of diagnosing bladder cancer in a subject comprising:
   obtaining a urine sample from a subject, wherein said sample comprises a plurality of bladder cells;
   detecting K17 expression in said bladder cells of said sample, wherein said detection comprises contacting said urine sample with an anti-K17 antibody, and detecting binding between K17 on said bladder cells and the anti-K17 antibody;
   obtaining a control urine sample comprising a plurality of bladder cells, wherein the control urine sample is a sample of urine from an individual free of bladder cancer;
   detecting K17 expression in said bladder cells of the control urine sample, wherein said detection comprises contacting the control urine sample with the anti-K17 antibody, and detecting binding between K17 on said bladder cells in the control urine sample and the anti-K17 antibody;
   diagnosing the subject with bladder cancer when between a 10-fold and a 60-fold increase in the amount of K17 expression is detected in the plurality of bladder cells of the subject when compared to the amount of K17 expression detected in the plurality of bladder cells of the control urine sample; and
   administering a treatment modality configured for the bladder cancer to the subject when between the 10-fold and the 60-fold increase in the amount of K17 expression is detected in the plurality of bladder cancer cells.

2. The method of claim 1, wherein said bladder cancer is urothelial carcinoma.

3. The method of claim 2, wherein said urothelial carcinoma is papillary neoplasia of low malignant potential, low-grade papillary urothelial carcinoma, high-grade papillary urothelial carcinoma or transitional-urothelial carcinoma.

4. The method of claim 1, wherein said anti-K17 antibody is a mouse monoclonal anti-K17 antibody.

5. The method of claim 1, wherein K17 expression in the plurality of bladder cells in the urine sample and the control urine sample is detected by a process selected from the group consisting of immunohistochemistry, microarray, western blotting, flow cytometry, microfluidics detection and enzyme-linked immunosorbent assay (ELISA).

6. The method of claim 5, wherein K17 expression in the plurality of bladder cells in the urine sample and the control urine sample is detected by immunohistochemistry.

7. A method for diagnosing a subject with bladder cancer comprising:
   obtaining a urine sample from a subject, wherein said urine sample comprises a plurality of bladder cells;
   detecting keratin 17 (K17) protein expression in said bladder cells of said urine sample from the subject, wherein said detection comprises:
      contacting said bladder cells with an anti-K17 antibody, and
      detecting binding between the K17 protein on said bladder cells in the urine sample and the anti-K17 antibody by immunohistochemical analysis or enzyme-linked immunosorbent assay (ELISA);
   obtaining a control urine sample comprising a plurality of bladder cells, wherein the control urine sample is a sample of urine from an individual free of bladder cancer;

detecting K17 protein expression in said bladder cells of the control urine sample, wherein said detection comprises:

contacting the bladder cells in the control urine sample with the anti-K17 antibody, and detecting binding between the K17 protein on said bladder cells in the control urine sample and the anti-K17 antibody by immunohistochemical analysis or ELISA; and diagnosing the subject with bladder cancer when between a 10-fold and a 60-fold increase in the amount of K17 expression is detected in the plurality of bladder cells of the subject when compared to the amount of K17 expression detected in the plurality of bladder cells of the control urine sample; and administering a treatment modality configured for the bladder cancer to the subject when between the 10-fold and the 60-fold increase in the amount of K17 expression is detected in the plurality of bladder cancer cells.

8. The method of claim 7, wherein said K17 protein expression is detected by ELISA.

9. The method of claim 7, wherein said anti-K17 antibody is a mouse anti-K17 antibody.

10. The method of claim 7, wherein the bladder cancer is a urothelial carcinoma selected from the group consisting of papillary neoplasia of low malignant potential, low-grade papillary urothelial carcinoma, high-grade papillary urothelial carcinoma and transitional-urothelial carcinoma.

* * * * *

SEQUENCE LISTING

<160> NUMBER OF SEQ ID NOS: 1

<210> SEQ ID NO 1
<211> LENGTH: 1731
<212> TYPE: DNA
<213> ORGANISM: Artificial Sequence
<220> FEATURE:
<223> OTHER INFORMATION: Synthetic construct

<400> SEQUENCE: 1

```
atggagcggg gaggagaagc ggcggcggcg gcggccgcgg cggctgcagc tccagggagg      60
gggtctgagt cgcctgtcac catttccagg gctgggaacg ccggagagtt ggtctctccc     120
cttctactgc ctccaacacg gcggcggcg cggcggcaca tccagggacc cgggccggtt      180
ttaaacctcc cgtccgccgc cgccgcaccc cccgtggccc gggctccgga ggccgccggc     240
ggaggcagcc gttcggagga ttattcgtct ctctccccatt ccgctgccgc cgctgccagg    300
cctctggctg ctgaggagaa gcaggcccag tcgctgcaac catccagcag ccgccgcagc     360
agccattacc cggctgcggt ccagagccaa gcggcggcag agcgaggggc atcagctacc     420
gccaagtcca gagccatttc catcctgcag aagaagcccg gccaccagca gcttctgcca     480
tctctctcct ccttttctctt cagccacagg ctcccagaca taacagccat catcaaagag     540
atcgttagca gaaacaaaag gagatatcaa gaggatggat tcgacttaga cttgacctat    600
```

-continued

```
atttatccaa acattattgc tatgggattt cctgcagaaa gacttgaagg cgtatacagg      660
aacaatattg atgatgtagt aaggtttttg gattcaaagc ataaaaacca ttacaagata      720
tacaatcttt gtgctgaaag acattatgac accgccaaat ttaattgcag agttgcacaa      780 tatcctttg aagaccataa cccaccacag ctagaactta tcaaaccctt ttgtgaagat       840
cttgaccaat ggctaagtga agatgacaat catgttgcag caattcactg taaagctgga      900
aagggacgaa ctggtgtaat gatatgtgca tatttattac atcggggcaa attttaaag      960 gcacaagagg ccctagattt ctatggggaa gtaaggacca gagacaaaaa gggagtaact     1020
attcccagtc agaggcgcta tgtgtattat tatagctacc tgttaaagaa tcatctggat     1080
tatagaccag tggcactgtt gtttcacaag atgatgtttg aaactattcc aatgttcagt     1140
ggcggaactt gcaatcctca gtttgtggtc tgccagctaa aggtgaagat atattcctcc     1200
aattcaggac ccacacgacg ggaagacaag ttcatgtact ttgagttccc tcagccgtta     1260
cctgtgtgtg gtgatatcaa agtagagttc ttccacaaac agaacaagat gctaaaaaag     1320
gacaaaatgt ttcacttttg ggtaaataca ttcttcatac caggaccaga ggaaacctca     1380
gaaaaagtag aaaatggaag tctatgtgat caagaaatcg atagcatttg cagtatagag     1440
cgtgcagata atgacaagga atatctagta cttactttaa caaaaaatga tcttgacaaa     1500
gcaaataaag acaaagccaa ccgatacttt tctccaaatt ttaaggtgaa gctgtacttc     1560
acaaaaacag tagaggagcc gtcaaatcca gaggctagca gttcaacttc tgtaacacca     1620
gatgttagtg acaatgaacc tgatcattat agatattctg acaccactga ctctgatcca     1680
gagaatgaac cttttgatga agatcagcat acacaaatta caaaagtctg a              1731
```